United States Patent
Igarashi

(10) Patent No.: US 9,622,652 B2
(45) Date of Patent: Apr. 18, 2017

(54) ENDOSCOPE OBJECTIVE OPTICAL SYSTEM

(71) Applicant: OLYMPUS CORPORATION, Tokyo (JP)

(72) Inventor: Tsutomu Igarashi, Tokyo (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 14/824,666

(22) Filed: Aug. 12, 2015

(65) Prior Publication Data
US 2015/0359422 A1 Dec. 17, 2015

Related U.S. Application Data

(63) Continuation of application No. PCT/JP2014/065815, filed on Jun. 13, 2014.

(30) Foreign Application Priority Data

Jun. 26, 2013 (JP) ................. 2013-133902

(51) Int. Cl.
*A61B 1/307* (2006.01)
*A61B 1/055* (2006.01)
*A61B 1/00* (2006.01)
*G02B 23/24* (2006.01)

(52) U.S. Cl.
CPC .......... *A61B 1/307* (2013.01); *A61B 1/00163* (2013.01); *A61B 1/00174* (2013.01); *A61B 1/055* (2013.01); *G02B 23/243* (2013.01)

(58) Field of Classification Search
CPC .. G02B 23/243; G02B 21/0028; G02B 23/24; G02B 13/04; G02B 9/04; G02B 9/10;
(Continued)

(56) References Cited

U.S. PATENT DOCUMENTS 5,087,989 A 2/1992 Igarashi
5,424,877 A * 6/1995 Tsuyuki ............. G02B 23/2407 359/663

(Continued)

FOREIGN PATENT DOCUMENTS

| JP | 02-277015 | 11/1990 |
|----|-----------|---------|
| JP | 05-288986 | 11/1993 |
| JP | 05-297272 | 11/1993 |
| JP | 05-323186 | 12/1993 |
| JP | 07-084180 | 3/1995 |
| JP | 08-122634 | 5/1996 |
| JP | 10-260348 | 9/1998 |
| JP | 10-288742 | 10/1998 |

(Continued)

OTHER PUBLICATIONS

International Search Report, dated Sep. 16, 2014, issued in corresponding International Application No. PCT/JP2014/065815.
(Continued)

*Primary Examiner* — Thomas K Pham
*Assistant Examiner* — Alberto Betancourt
(74) *Attorney, Agent, or Firm* — Andrew Kurth Kenyon LLP

(57) ABSTRACT

An endoscope objective optical system comprises:
a front group having a negative refractive power, a brightness diaphragm, and a back group having a positive refractive power in order from an object side, wherein
the front group is composed of a first group, which is a first lens which is a single lens and a second group, which is a single lens or a cemented lens having a negative refractive power;

$1 < Iw/ft < 1.8$ $0.6 < Ia/Iw < 0.95$ $|DL1/RL1a| < 0.4$ $-3 < fL1/ft < -1$ where Iw is a maximum image height in underwater observation, ft is a focal distance of an entire objective optical system in observation in the air, Ia is a maximum image height capable of transmitting a principal ray in the observation in the air, and DL1, RL1a, and fL1 are an outer diameter, a radius of curvature of an object side surface, and a focal distance, respectively of the first lens.

1 Claim, 29 Drawing Sheets

(58) Field of Classification Search
CPC ..... G02B 9/12; G02B 9/58; G02B 9/60–9/64; A61B 1/307; A61B 1/00174
USPC .......... 359/656–661, 749–753; 600/101–183
See application file for complete search history.

(56) References Cited

U.S. PATENT DOCUMENTS

| | | | |
|---|---|---|---|
| 5,576,882 | A | 11/1996 | Kanamori |
| 5,980,453 | A * | 11/1999 | Forkey ............... A61B 1/00193 600/162 |
| 2008/0080061 | A1* | 4/2008 | Miyano ............... G02B 23/243 359/661 |
| 2013/0155212 | A1 | 6/2013 | Kamo |

FOREIGN PATENT DOCUMENTS

| | | |
|---|---|---|
| JP | 2002-116491 | 4/2002 |
| JP | 2008-089658 | 4/2008 |
| JP | 4819203 | 11/2011 |

OTHER PUBLICATIONS

Extended European Search Report, dated Dec. 1, 2016, from corresponding European Application No. 14817759.5.

* cited by examiner

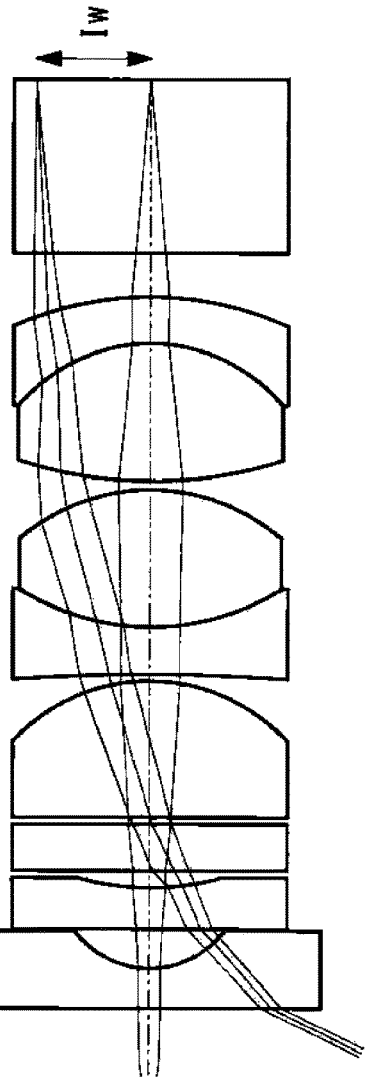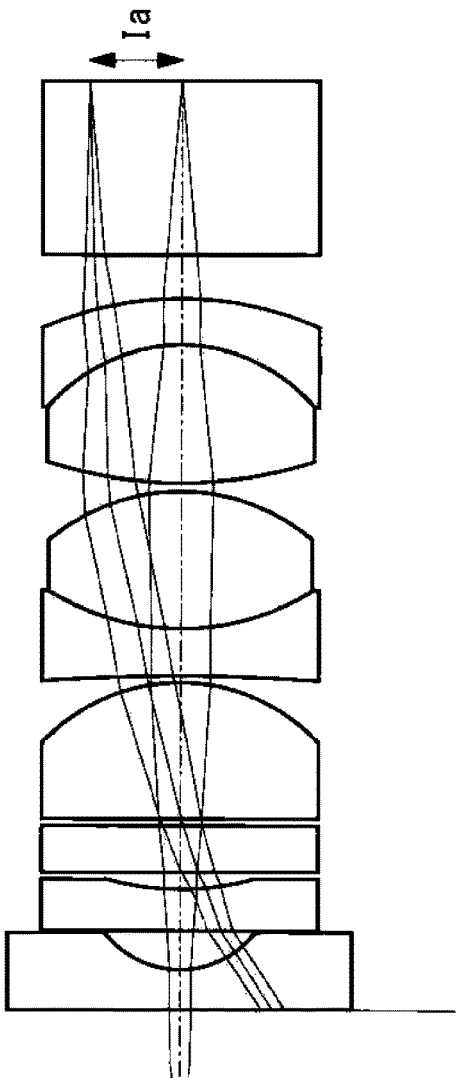
FIG. 4A UNDERWATER
FIG. 4B IN AIR

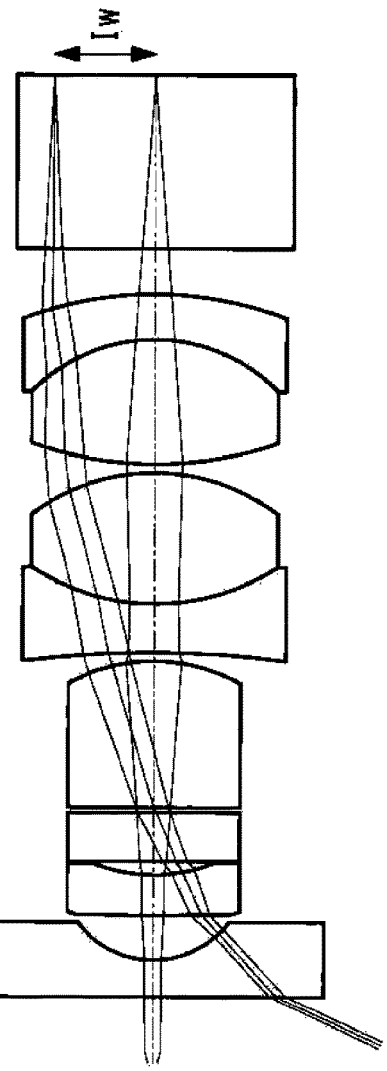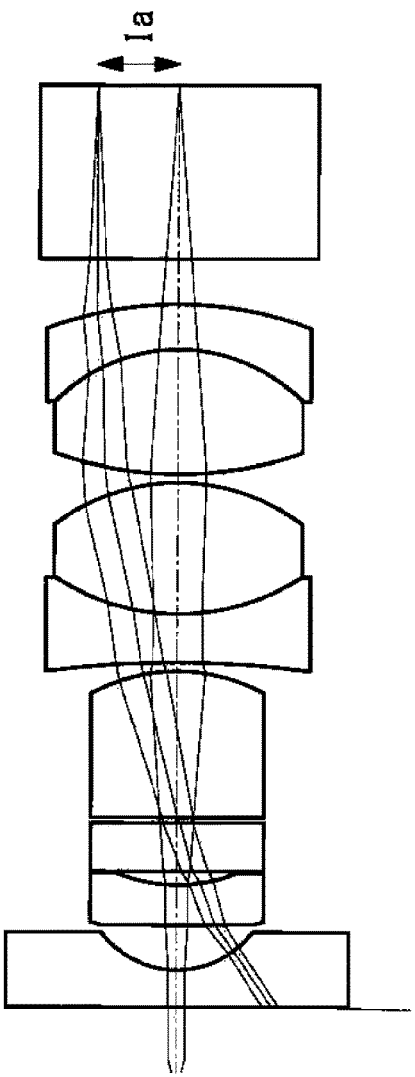
FIG. 7A UNDERWATER   FIG. 7B IN AIR

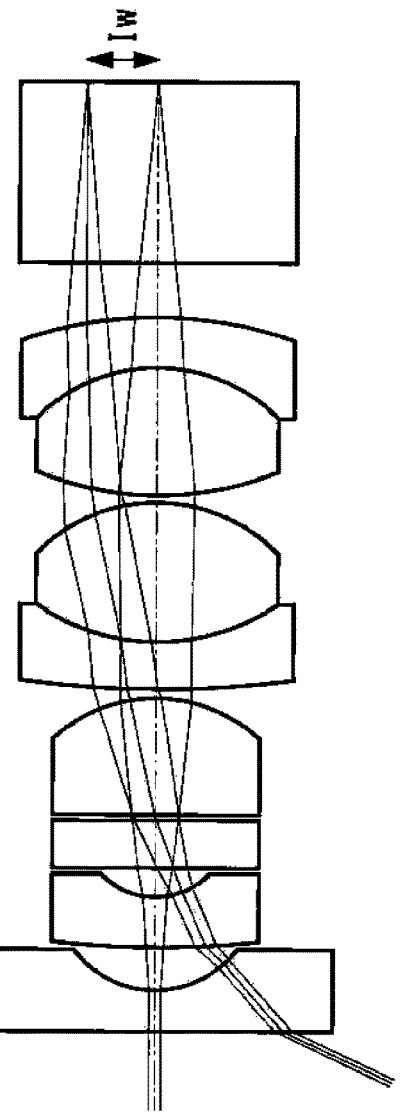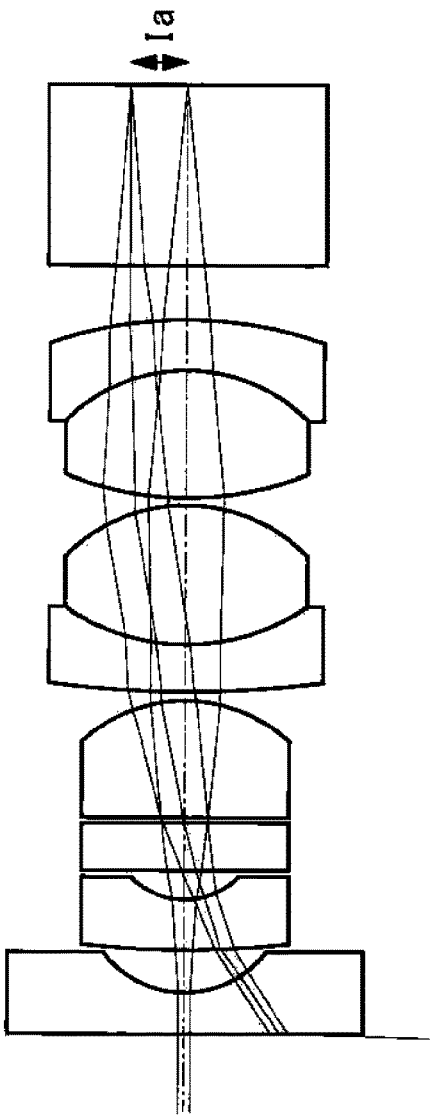
FIG. 10A UNDERWATER
FIG. 10B IN AIR

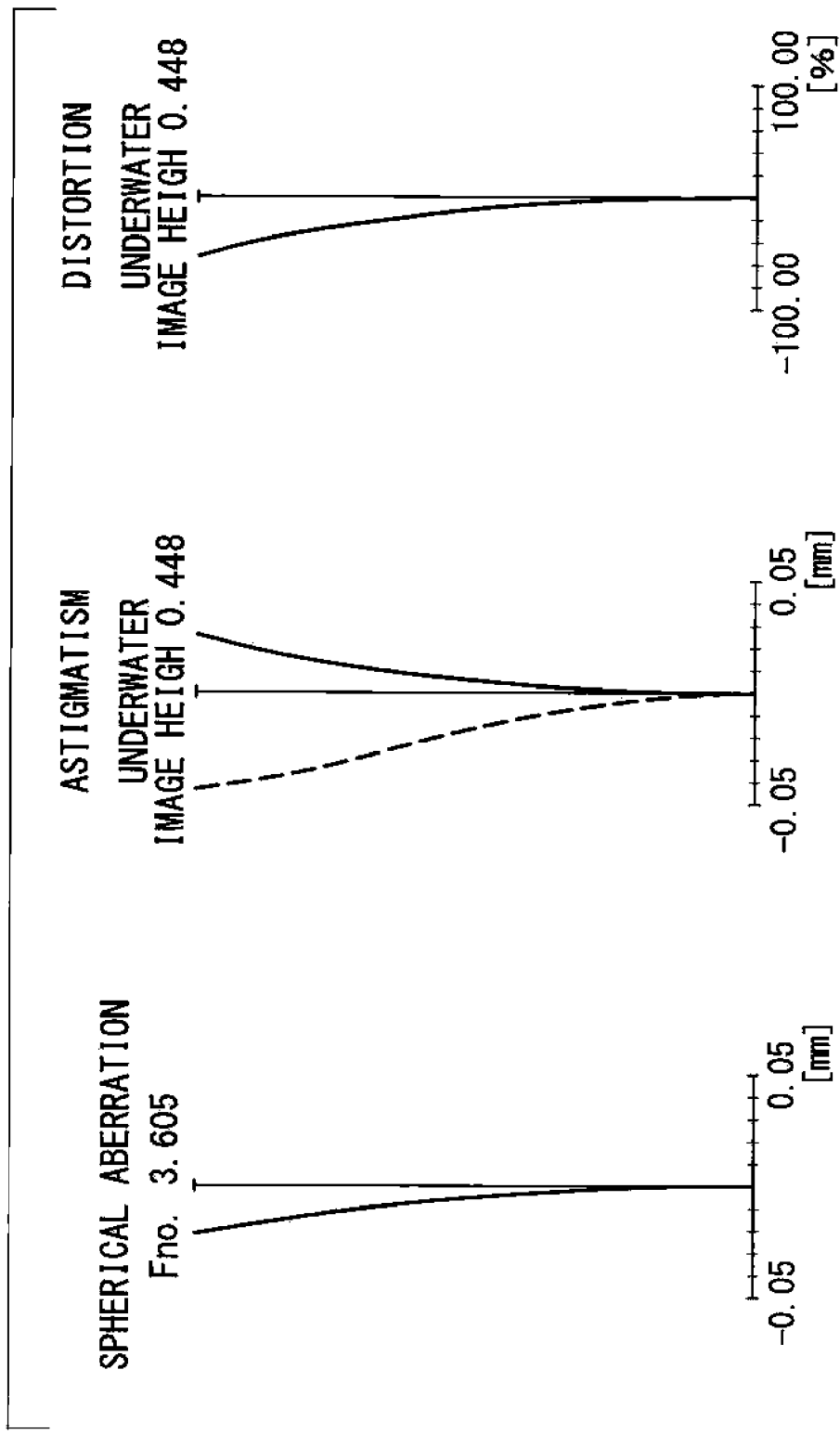

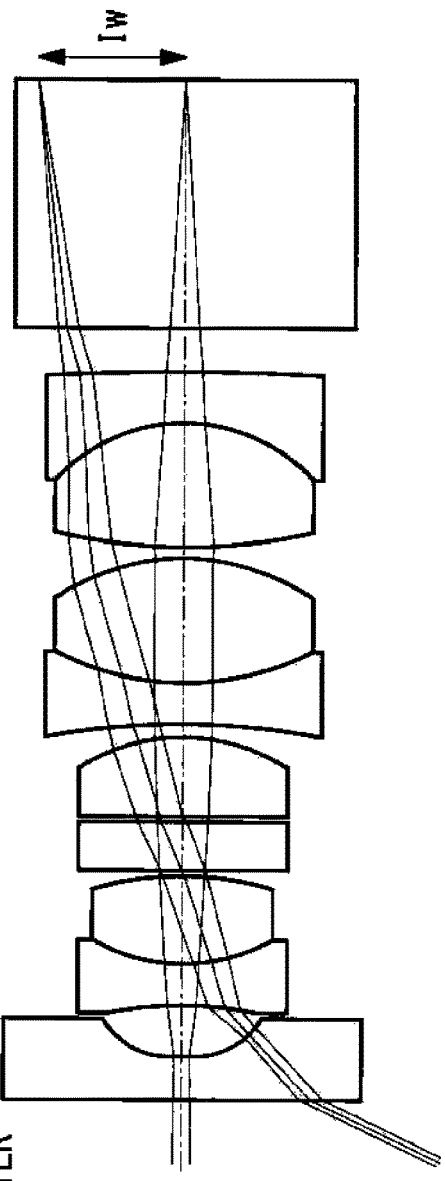
FIG. 13A UNDERWATER
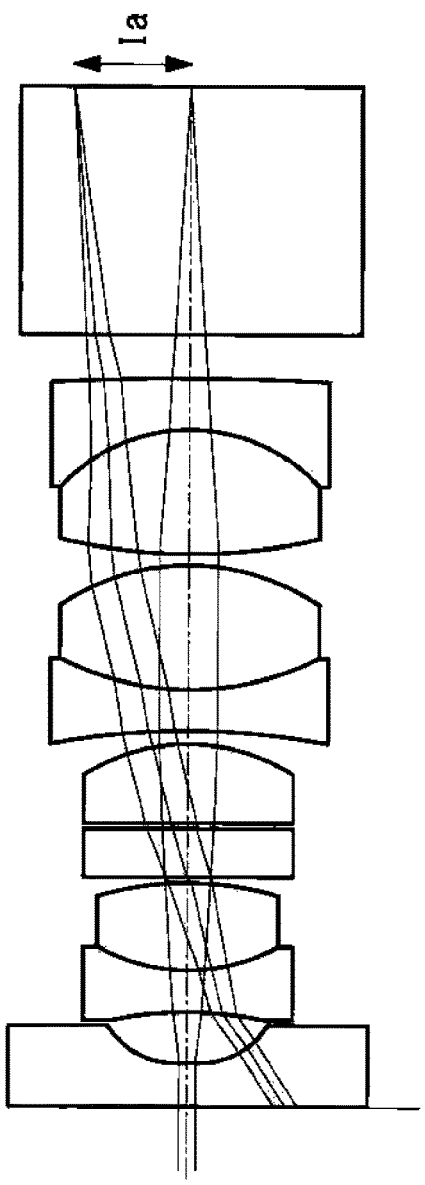
FIG. 13B IN AIR

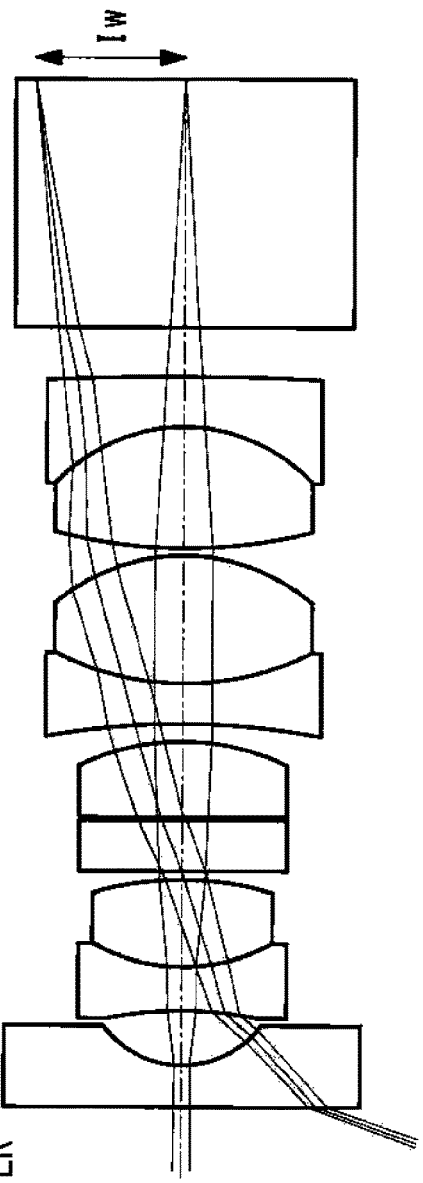
FIG. 16A UNDERWATER
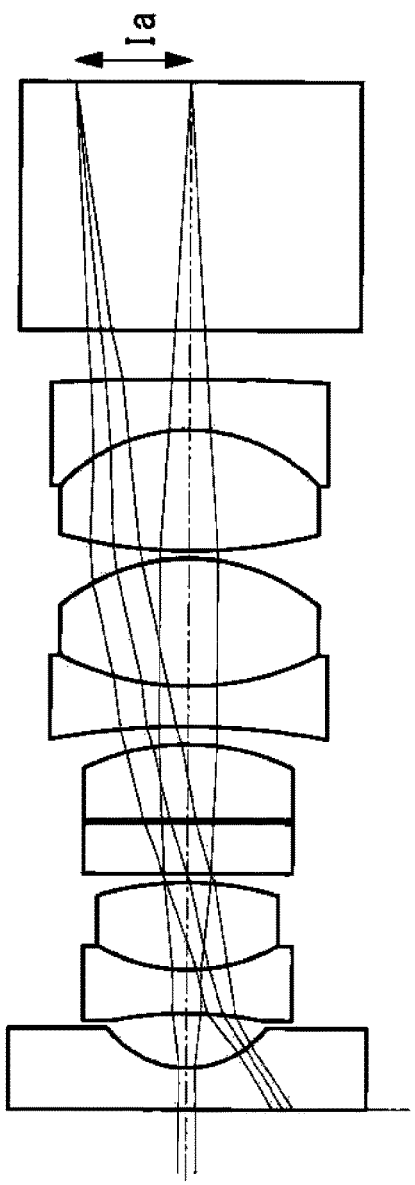
FIG. 16B IN AIR

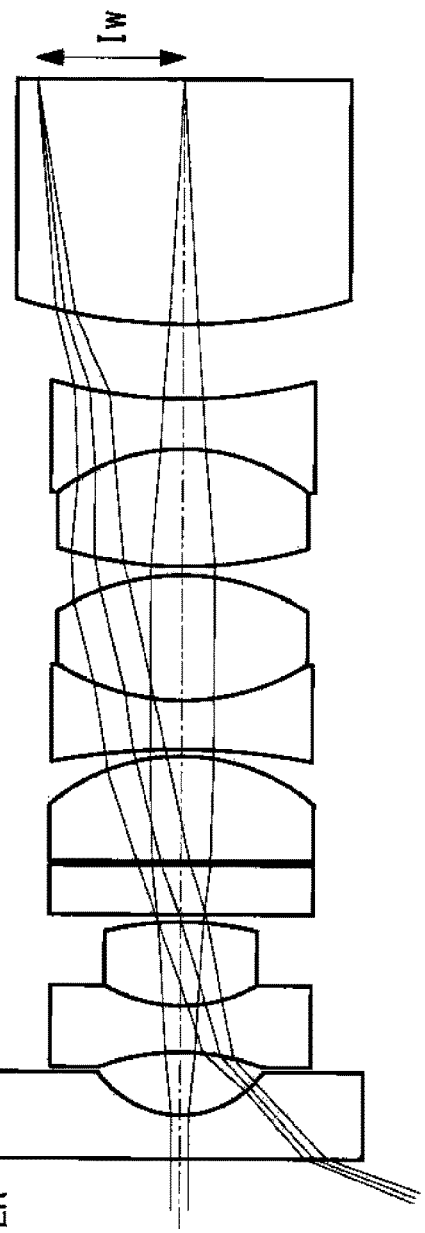
FIG. 19A UNDERWATER
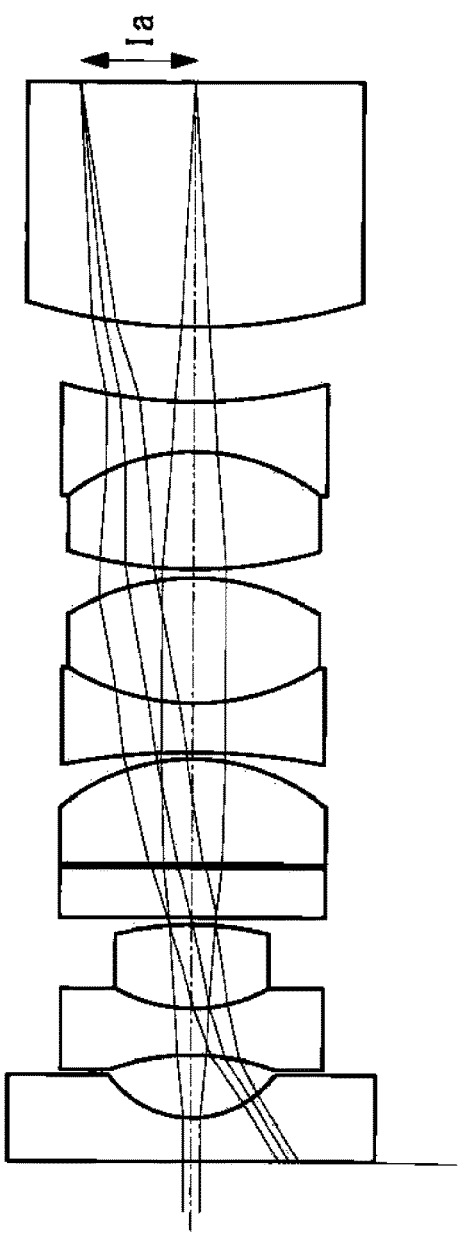
FIG. 19B IN AIR

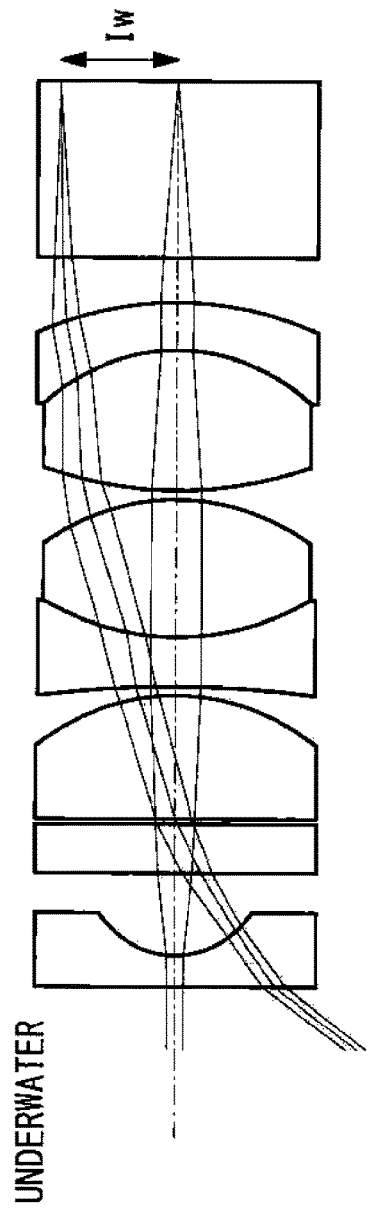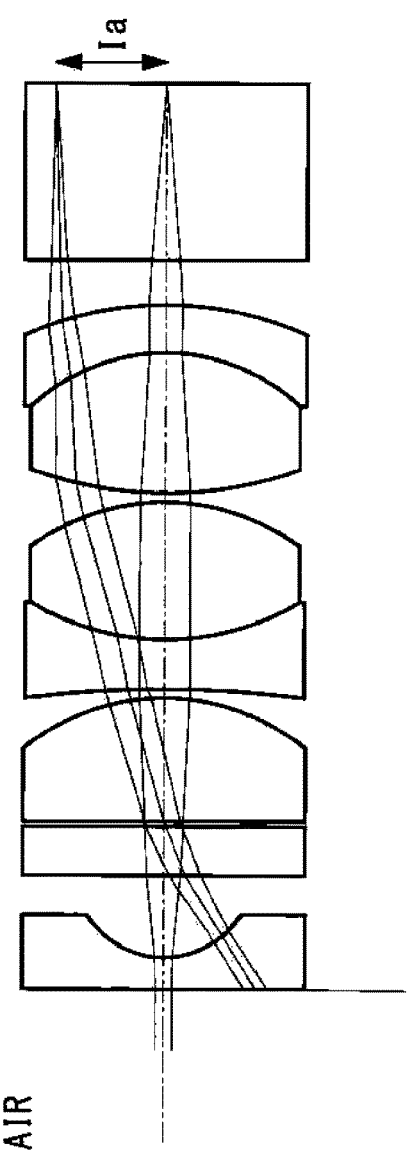
FIG. 22A UNDERWATER
FIG. 22B IN AIR

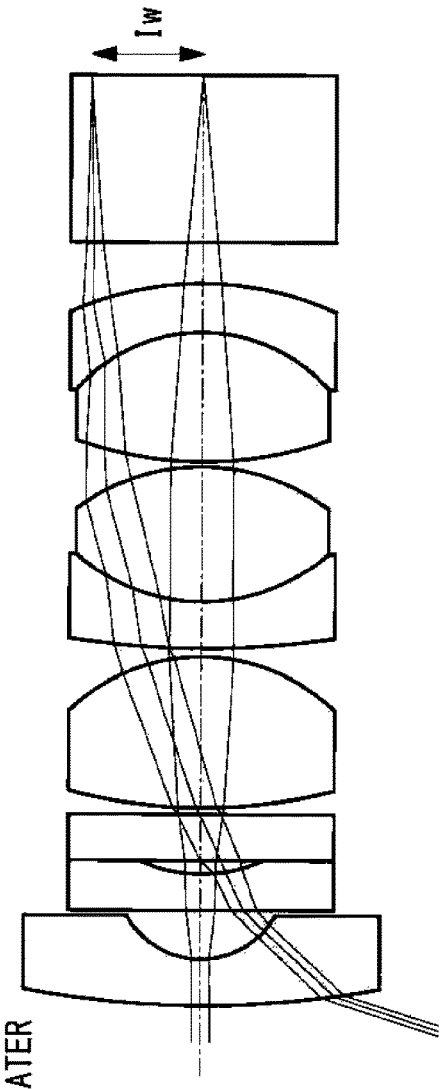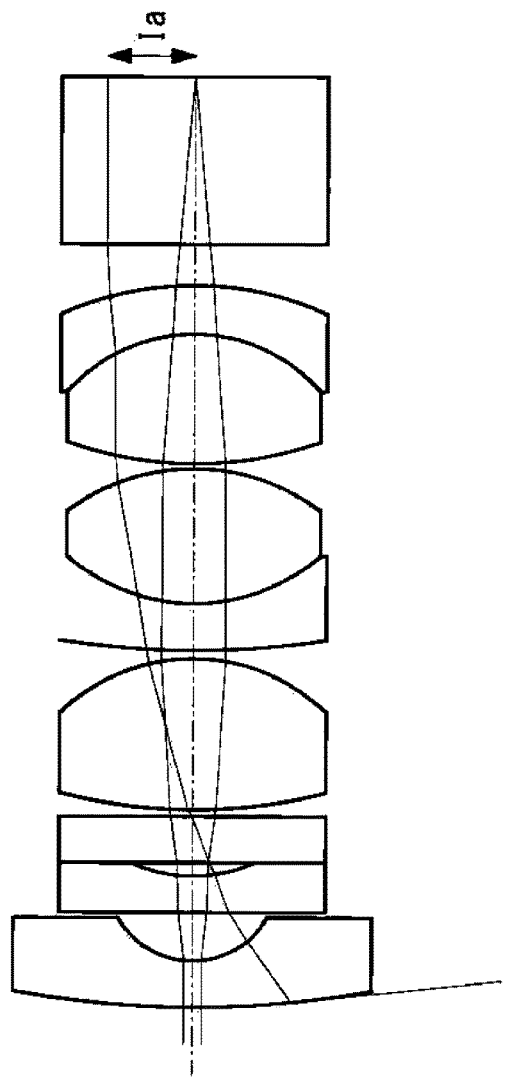
FIG. 25A UNDERWATER
FIG. 25B IN AIR

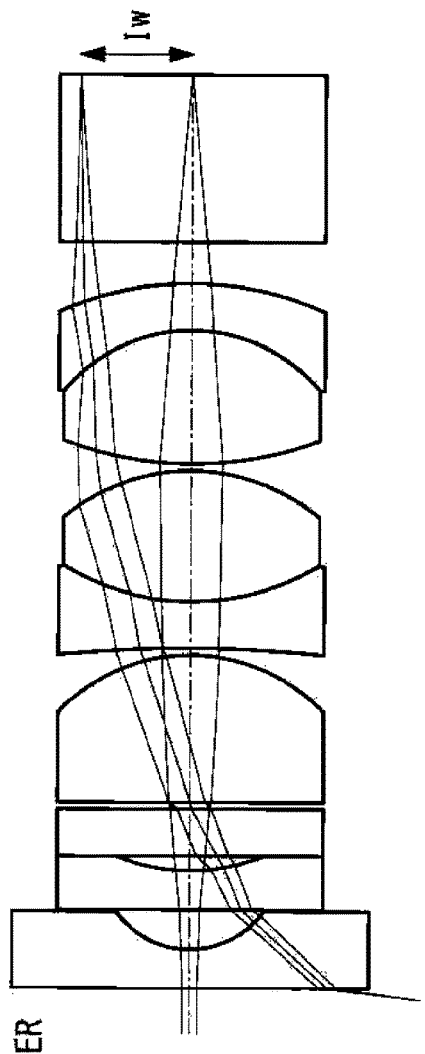
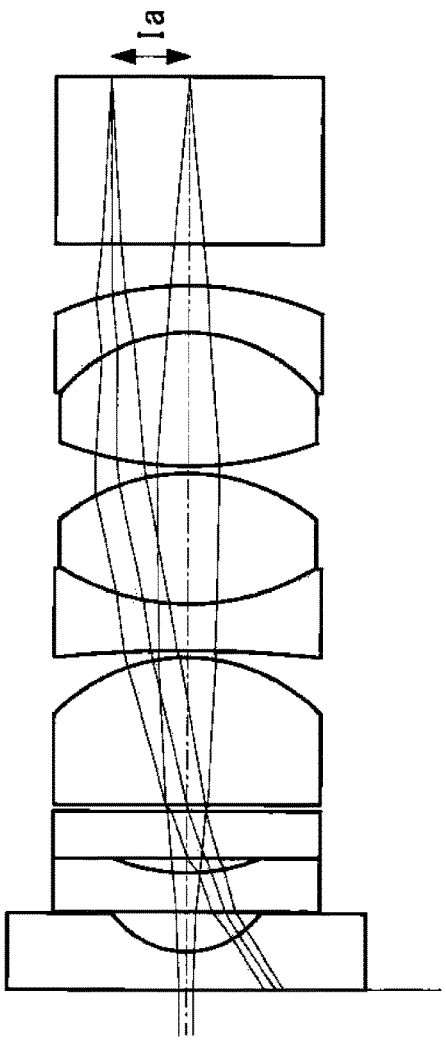
FIG. 28A UNDERWATER
FIG. 28B IN AIR

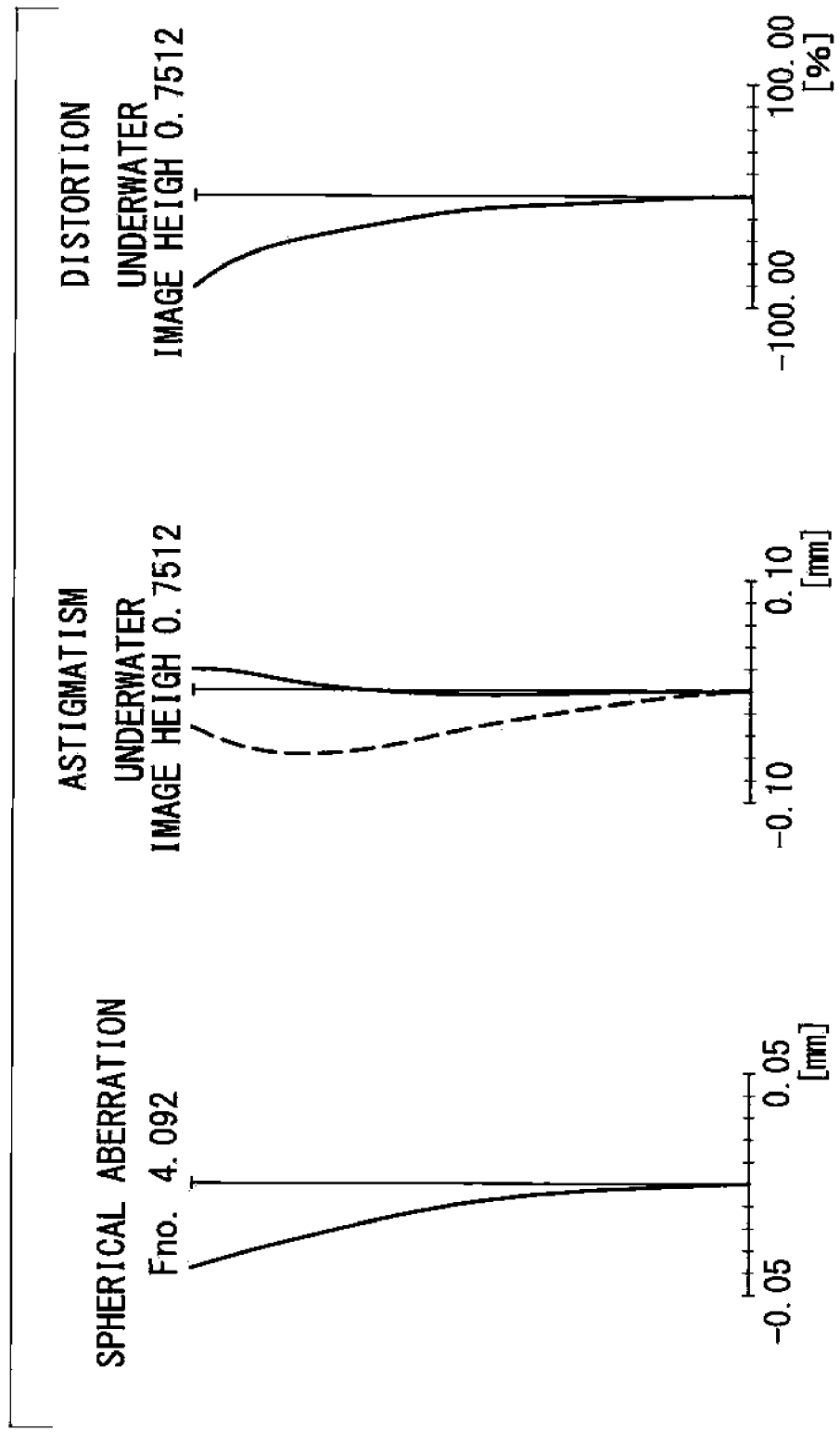

ENDOSCOPE OBJECTIVE OPTICAL SYSTEM

CROSS-REFERENCE TO RELATED APPLICATIONS

This application is a Continuation Application of International Application PCT/JP2014/065815 filed on Jun. 13, 2014, which claims priority to Japanese Application No. 2013-133902 filed on Jun. 26, 2013.

The Contents of International Application PCT/JP2014/065815 and Japanese application No. 2013-133902 are hereby incorporated by reference herein in its entirety.

TECHNICAL FIELD

The present invention relates to an endoscope objective optical system applied to a medical endoscope.

BACKGROUND ART

If urinary organs are to be observed by an endoscope, an observation space is filled with urine, for example, and a relatively transparent visual field is ensured by causing a perfusate such as a saline to perfuse. The perfusate and urine are both composed mainly of water, and concentrations of a salt, a sugar and the like are not so high and thus, refractive indexes can be considered to be equal to that of water. Thus, in endoscopes intended for observation of these organs, optical specification/performance in underwater observation regarding an object-side medium as water determines practicability.

A point requiring an utmost attention in the endoscope objective optical system for underwater observation is angle narrowing of an underwater view angle with respect to that in an air. A d-line refractive index of water is 1.333 at a normal temperature, and a relationship between the view angle in the air and the underwater view angle when an outer surface of the endoscope objective optical system is a plane is illustrated below:

| View angle in the air | 180° | 160° | 140° | 120° |
|---|---|---|---|---|
| Underwater view angle | 97.2° | 95.3° | 89.7° | 81.0° |

Using an endoscope for bladder as an example, even if a view angle in the air is relatively wide at 120°, an underwater view angle in actual observation in the bladder is 81°, and a view field range is considerably narrower in the water. In order to search a lesion over the whole region of a bladder inner surface, an operator performs an operation combining operations of curving of a tip end of the endoscope, insertion/removal of an insertion portion, and twisting of the insertion portion, but if the underwater view angle is small, frequencies of these operations are increased, which is not desirable from a view point of work efficiency. By widening the underwater view angle, a burden on an endoscopic operation of the operator can be reduced, and improvement of efficiency of diagnosis/treatment can be expected. Thus, as an objective optical system relating to underwater observation or wide-angle observation of an endoscope, for example, the objective optical system with the view angle in the air at 138.3° at the maximum is disclosed in PTL 1, the objective optical system with the view angle in the air at 180° or more is disclosed in PTL 2, and the objective optical system with the view angle in the air at 190° to 227° is disclosed in PTL 3, respectively.

CITATION LIST

Patent Literature

{PTL 1}
Japanese Unexamined Patent Application, Publication No. 5-288986
{PTL 2}
Japanese Unexamined Patent Application, Publication No. 10-288742
{PTL 3}
the Publication of Japanese Patent No. 4819203

SUMMARY OF INVENTION

Technical Problem

However, each of the aforementioned Patent Literatures has the following problems.

That is, in the objective optical system of PTL 1, though the view angle in the air is wide, if it is converted to a value in the water by using the Snell's law on the basis of the fact that the first plane is planar, the underwater view angle is 89°, which is not a sufficient view angle in practice.

In the objective optical system in PTL 2, a first lens of the objective optical system is a concave meniscus lens having a strong convex surface on an object side, and with such a shape, the lens can be easily damaged such as a scratch or a crack due to an unexpected object collision. A devise of protruding a frame for preventing breakage of the first lens is disclosed, but with this constitution, illumination light is shielded by a frame protruding portion, which deteriorates light distribution. Moreover, in the constitution having a step between the frame and the lens, removal of stains on the step portion is difficult, and in the case of a medical use, problems of cleaning/sterilization/disinfection are caused. On the other hand, in order to improve resistance against scratches/cracks, a highly hard optical material such as sapphire needs to be used for the material of the first lens, but highly hard optical material has poor workability in general, and machining difficulty is high for the concave meniscus shape with largely protruding convex surface.

Moreover, in the frame structure in the objective optical system of PTL 2, the concave meniscus first lens is dented from the object side, and this lens fixing structure has a problem in ensuring reliability as a medical use. That is, if an adhesive is used for fixing the first lens, deterioration of the adhesive caused by a chemical factor or a temperature/humidity is accumulated more or less by repetition of sterilization/disinfection at each use for the medical use, and thus, there is a concern that the lens drops to the object side due to the accumulation of deterioration. On the other hand, soldering can be used as a lens fixing method more reliable than the adhesive, but there is a concern of breakage of the lens by a contraction stress during solidification of a solder in the concave meniscus lens, and a soldering structure cannot be employed easily.

Moreover, in PTL 2, since an optical axis of an illumination optical system is tilted outward, diameter reduction of an outer diameter of a tip end is difficult. If diameter reduction takes priority, and the optical axis of the illumination optical system is made parallel with the objective optical system, occurrence of flare caused by direct incidence of illumination light to the largely protruding convex surface of the objective optical system is expected.

The objective optical system in PTL 3 has a problem similar to that of the aforementioned objective optical system of PTL 2 since a tip end surface of the objective optical system is a strong convex surface.

The present invention was made in view of the aforementioned circumstances and has an object to provide an objective optical system which has a wide view angle even in underwater observation and facilitates a mounting design while reliability as a medical endoscope is ensured.

Solution to Problem

In order to achieve the aforementioned object, the present invention provides the following solutions:

An aspect of the present invention provides an endoscope objective optical system used for underwater observation, comprising:

a first group having a negative refractive power on an object side, wherein the first group is a first lens which is a single lens; and conditional expressions below are satisfied:

$$1 < Iw/ft < 1.8 \tag{1}$$

$$0.6 < Ia/Iw < 0.95 \tag{2}$$

$$|DL1/RL1a| < 0.4 \tag{3}$$

$$-3 < fL1/ft < -1 \tag{4}$$

where Iw is a maximum image height in underwater observation, ft is a focal distance of the entire objective optical system in observation in the air, and Ia is a maximum image height capable of transmitting a principal ray in the observation in the air, DL1 is an outer diameter of the first lens, RL1a is a radius of curvature of an object side surface of the first lens, and fL1 is a focal distance of the first lens.

The aforementioned expression (1) is a condition relating to a view angle in the underwater observation, and a right-side inequality expression (Iw/ft<1.8) in the expression (1) is to avoid excessive widening of an angle in the underwater observation. If Iw/ft falls under a lower limit of the expression (1), the underwater view angle becomes narrow and insufficient, while if an upper limit is exceeded, the underwater view angle becomes too wide and lower brightness in an image peripheral portion (insufficient light distribution on an illumination optical system side and lower light amount in the periphery of the objective optical system) is caused.

The expression (2) is a condition regulating a relationship of the maximum image heights in the underwater observation and in the observation in the air, and if the upper limit of the expression (2) is exceeded, widening of the underwater view angle obtained in compensation for the observation in the air is not sufficient, which is not desirable. On the other hand, if the lower limit of the expression (2) is not reached, an effective image area in the observation in the air is excessively small, and defective light control or trouble in detection of a peripheral image defect is caused in obtainment of white balance or in assembly/quality tests in manufacture.

Therefore, according to this aspect, a view angle is wide also in the underwater observation, reliability as a medical endoscope is ensured, and mounting design can be made easily.

The aforementioned expression (3) is a condition for a constitution that a degree of convex and concave on the first lens object side surface is made small and relatively close to a plane. If the first group is made of flat plates, for example, a light beam can be transmitted through an image side surface of a flat plate in contact with the air has the same angle as that of the object side surface in a state of observation in the air and thus, Iw cannot be made larger than Ia. Since a light flux at an extremely large angle passes through the first group, a lens thickness is closely related with a light beam height, and if the thickness is increased, the lens outer diameter is increased. Thus, it is necessary that use of cemented lenses which increases the lens thickness is avoided so as to promote thinning by using a single lens for the first group.

If the upper limit of the aforementioned expression (3) is exceeded on the convex surface, the convex from a lens outer diameter end becomes too large, and a mechanical design to avoid lens breakage or illumination light incidence becomes difficult. Moreover, if the upper limit of the aforementioned expression (3) is exceeded on the concave surface, the concave from the lens outer diameter end becomes too large, and deterioration in cleaning performance or an increase of Fresnel reflective rate in the peripheral portion of the concave surface occur.

The expression (4) is a condition relating to the focal distance of the first lens. In order to make Iw larger than Ia in relation with the expression (2), power of the first lens needs to be negative, and an absolute amount of the power has an appropriate range. If the lower limit of the expression (4) is not reached, the power is too weak to realize angle widening in the water, while if the upper limit of the expression (4) is exceeded, and the negative power is so strong that an excessive correction tendency of field curvature is caused.

BRIEF DESCRIPTION OF DRAWINGS

FIG. 2A and FIG. 2B are conceptual diagrams illustrating image pickup ranges of underwater observation and observation in an air by the endoscope objective optical system according to the first embodiment of the present invention, in which FIG. 2A illustrates a state of the underwater observation.

FIG. 2A and FIG. 2B are conceptual diagrams illustrating image pickup ranges of underwater observation and observation in an air by the endoscope objective optical system according to the first embodiment of the present invention, in which FIG. 2B illustrates a state of the observation in the air.

FIG. 4A and FIG. 4B are sectional views illustrating the entire constitution of the endoscope objective optical system according to the first example of the present invention, in which FIG. 4A illustrates the state of the underwater observation.

FIG. 4A and FIG. 4B are sectional views illustrating the entire constitution of the endoscope objective optical system according to the first example of the present invention, in which FIG. 4B illustrates the state of the observation in the air.

FIG. 7A and FIG. 7B are sectional views illustrating the entire constitution of the endoscope objective optical system according to the second example of the present invention, in which FIG. 7A illustrates the state of the underwater observation.

FIG. 7A and FIG. 7B are sectional views illustrating the entire constitution of the endoscope objective optical system according to the second example of the present invention, in which FIG. 7B illustrates the state of the observation in the air.

FIG. 10A and FIG. 10B are sectional views illustrating the entire constitution of the endoscope objective optical system according to the third example of the present invention, in which FIG. 10A illustrates the state of the underwater observation.

FIG. 10A and FIG. 10B are sectional views illustrating the entire constitution of the endoscope objective optical system according to the third example of the present invention, in which FIG. 10B illustrates the state of the observation in the air.

FIG. 11 is an aberration diagram of the state of the underwater observation of the endoscope objective optical system according to the third example of the present invention.

FIG. 13A and FIG. 13B are sectional views illustrating the entire constitution of the endoscope objective optical system according to the fourth example of the present invention, in which FIG. 13A illustrates the state of the underwater observation.

FIG. 13A and FIG. 13B are sectional views illustrating the entire constitution of the endoscope objective optical system according to the fourth example of the present invention, in which FIG. 13B illustrates the state of the observation in the air.

FIG. 16A and FIG. 16B are sectional views illustrating the entire constitution of the endoscope objective optical system according to the fifth example of the present invention, in which FIG. 16A illustrates the state of the underwater observation and FIG. 16B illustrates the state of the observation in the air.

FIG. 16A and FIG. 16B are sectional views illustrating the entire constitution of the endoscope objective optical system according to the fifth example of the present invention, in which FIG. 16B illustrates the state of the observation in the air.

FIG. 19A and FIG. 19B are sectional views illustrating the entire constitution of the endoscope objective optical system according to the sixth example of the present invention, in which FIG. 19A illustrates the state of the underwater observation.

FIG. 19A and FIG. 19B are sectional views illustrating the entire constitution of the endoscope objective optical system according to the sixth example of the present invention, in which FIG. 19B illustrates the state of the observation in the air.

FIG. 22A and FIG. 22B are sectional views illustrating the entire constitution of the endoscope objective optical system according to the seventh example of the present invention, in which FIG. 22A illustrates the state of the underwater observation.

FIG. 22A and FIG. 22B are sectional views illustrating the entire constitution of the endoscope objective optical system according to the seventh example of the present invention, in which FIG. 22B illustrates the state of the observation in the air.

FIG. 25A and FIG. 25B are sectional views illustrating the entire constitution of the endoscope objective optical system according to the eighth example of the present invention, in which FIG. 25A illustrates the state of the underwater observation.

FIG. 25A and FIG. 25B are sectional views illustrating the entire constitution of the endoscope objective optical system according to the eighth example of the present invention, in which FIG. 25B illustrates the state of the observation in the air.

FIG. 28A and FIG. 28B are sectional views illustrating the entire constitution of the endoscope objective optical system according to the ninth example of the present invention, in which FIG. 28A illustrates the state of the underwater observation.

FIG. 28A and FIG. 28B are sectional views illustrating the entire constitution of the endoscope objective optical system according to the ninth example of the present invention, in which FIG. 28B illustrates the state of the observation in the air.

FIG. 29 is an aberration diagram of the state of the underwater observation of the endoscope objective optical system according to the ninth example of the present invention.

DESCRIPTION OF EMBODIMENTS

First Embodiment

An endoscope objective optical system according to a first embodiment of the present invention will be described below by referring to the attached drawings.

Figure 1:
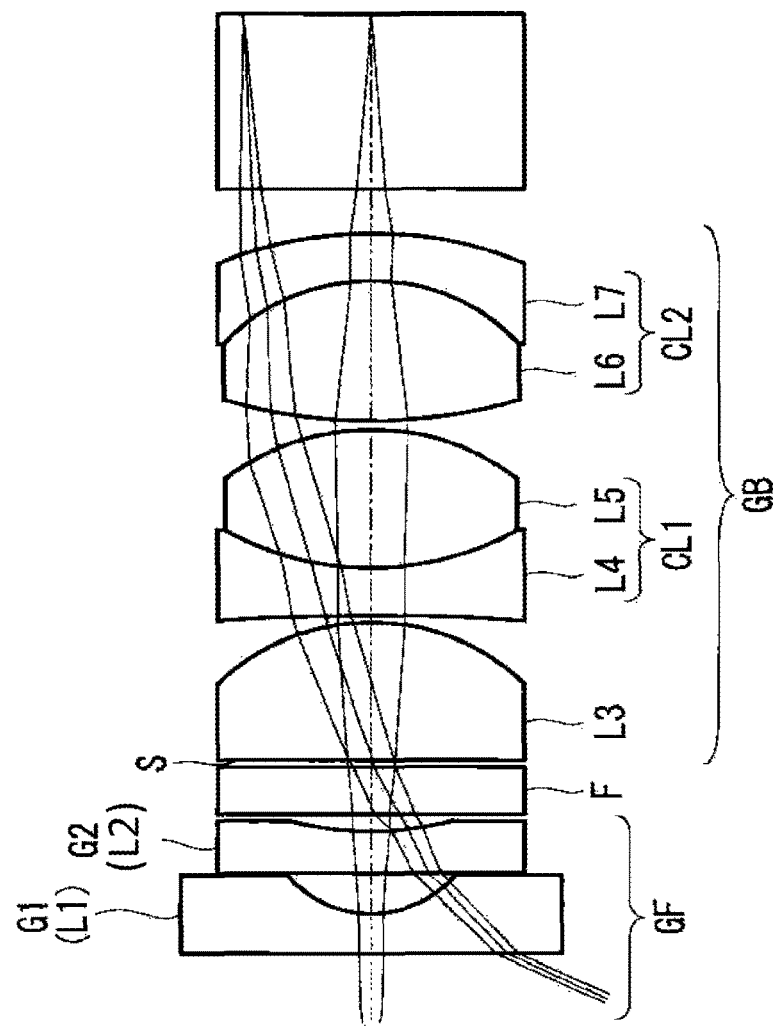
FIG. 1 is a sectional view illustrating an entire constitution of an endoscope objective optical system according to a first embodiment of the present invention.

FIG. 1 is a sectional view illustrating an entire constitution of the endoscope objective optical system. As illustrated in FIG. 1, the endoscope objective optical system includes a front group GF having a negative refractive power, a brightness diaphragm S, and a back group GB having a positive refractive power in order from an object side.

The front group GF includes a first lens L1 as a first lens group, and a second lens L2 as a second lens group G2 in order from the object side surface. The first lens L1 and the second lens L2 are plano-concave lenses each having a planar object side surface. In FIG. 1, a color correction filter F is provided between the front group GF and the brightness diaphragm S.

The back group GB includes a third lens L3, a cemented lens CL1 in which a fourth lens L4 and a fifth lens L5 are cemented, and a cemented lens CL2 in which a sixth lens L6 and a seventh lens L7 are cemented. The third lens L3, the cemented lens CL1, and the cemented lens CL2 all have the positive refractive power.

Moreover, the endoscope objective optical system is constituted so as to satisfy the following conditional expressions:

$$1 < Iw/ft < 1.8 \quad (1)$$

$$0.6 < Ia/Iw < 0.95 \quad (2)$$

where Iw is a maximum image height in underwater observation, ft is a focal distance of the entire objective optical system in observation in the air, and Ia is a maximum image height capable of transmitting a principal ray in the observation in the air.

The expression (1) is a condition relating to a view angle in the underwater observation. Reference character ft which is a focal distance of the entire objective optical system is varied by an influence of an object-side medium if a first surface on the object side has a curvature and thus, a distance when the object side medium is air is assumed to be a focal distance similarly to definition of a general lens focal distance.

As Iw/ft becomes smaller, an underwater view angle becomes smaller, while as Iw/ft becomes larger, the underwater view angle becomes larger. In the endoscope objective optical system designed for observation in the air, an objective optical system of so-called $H=ft*\sin(\theta a)$ type in which an image height H is in proportion to the focal distance ft and sine of a principal ray incident angle $\theta a$ in the air is known, and H/ft is 1 or less.

In comparison, a left-side inequality expression (Iw/ft>1) in the expression (1) means that the maximum image height in the underwater observation is taken larger than an image height presumed in the observation in the air, which contributes to angle widening in the underwater observation. Moreover, a right-side inequality expression (Iw/ft<1.8) in the expression (1) is to avoid excessive widening of an angle in the underwater observation. If Iw/ft falls under a lower limit of the expression (1), the underwater view angle becomes narrow and insufficient, while an upper limit is exceeded, the underwater view angle becomes too wide and lower brightness in an image peripheral portion (insufficient light distribution on an illumination optical system side and lower light amount in the periphery of the objective optical system) is caused, which is not desirable.

The expression (2) is a condition regulating a relationship of the maximum image height in the underwater observation and the observation in the air. If Ia/Iw is smaller than 1, it corresponds to a fact that a size of a usable image in the observation in the air is smaller than that in the underwater observation. An image range between Ia and Iw is a region that the principal ray incident from an object space cannot reach in the observation in the air, but a normal image of the object space filled with water is formed in the underwater observation. An estimation result of Ia/Iw using a maximum value of an underwater principal ray incident angle $\theta w$ as a variable is shown in Table below. However, estimation conditions are as follows:

Outer Surface of Endoscope Objective Optical System: Plane d-line refractive index of water: nw=1.333

Projection expression of objective optical system in observation in the air: Image height in the air $Ha=ft*\sin(\theta a)$ Projection expression of objective optical system in underwater observation: Underwater image height $Hw=ft*nw*\sin(\theta w)$ ft=1 (for facilitation of calculation)

$Ia=ft*\sin(\theta a\ \text{maximum value})=ft*\sin(90°)=1$

TABLE 1

| | $\theta w$ MAXIMUM VALUE [°] | | | | | | | |
|---|---|---|---|---|---|---|---|---|
| | 48.61 | 50 | 55 | 60 | 65 | 70 | 75 | 80 |
| Iw | 1 | 1.021 | 1.092 | 1.154 | 1.208 | 1.253 | 1.288 | 1.313 |
| Ia/Iw | 1 | 0.979 | 0.916 | 0.866 | 0.828 | 0.798 | 0.777 | 0.762 |

Description will be made by using $\theta w=70°$ in Table above (underwater view angle: 140°) as an example. The objective optical system designed for an underwater view angle at 140° based on the aforementioned condition is a so-called fish-eye lens with a view angle in the air at 180° at an image height of a ratio at 79.8% to an image height in the underwater observation, and an image from the object space in the air cannot be formed within an image range outside of it.

As described above, by making Ia/Iw smaller than 1 and by allowing a peripheral image defect in the observation in the air more or less, the underwater view angle can be widened. Such a design idea is not suitable for an endoscope for the observation in the air but it is practical enough for an endoscope for the underwater observation. Moreover, by lifting a limitation of ensuring of an image range for the observation in the air equal to that for the underwater observation, it is no longer necessary to give a strong convex surface on the lens tip end surface, and a great merit that various problems caused by the strong convex surface can be solved can be obtained.

Works requiring consideration of the observation state in the air include obtainment of white balance by image pickup of a white object and assembly/quality tests in manufacture, though they are not genuine medical acts. Thus, an attention needs to be paid to a trend that Ia/Iw is made too small.

At the upper limit of the expression (2) or more, widening of an underwater view angle obtained as compensation for the observation in the air is not sufficient, which is not desirable. At the lower limit of the expression (2) or less, an effective image area in the observation in the air becomes too small, and defective light control or trouble in detection of a peripheral image defect is caused in obtainment of white balance or in assembly/quality tests in manufacture, which is not desirable.

Moreover, the endoscope objective optical system preferably satisfies the following expression (3):

$$|DL1/RL1a|<0.4 \quad (3)$$

where DL1 is an outer diameter of the first lens, and RL1$a$ is a radius of curvature of the object side surface of the first lens.

The first lens group located the closest to the object side needs to have a negative refractive power in relation with satisfaction of the aforementioned expression (2). If the first lens is made of a flat plate, for example, since the light beam capable of being transmitted through the flat-plate image side surface in contact with the air has the same angle as that on the object side surface in the state of the observation in the air, Iw cannot be made larger than Ia.

Since a light flux having an extremely large angle passes through the first lens group, a lens thickness is deeply related with the light beam height, and if the thickness is increased, the lens outer diameter is increased. Thus, use of a cemented lens which increases the lens thickness for the first lens group needs to be avoided so as to realize thinning with a single lens.

In order to realize the above, the expression (3) is a condition for obtaining a constitution close to a relatively flat plane by reducing a degree of convex and concave on the first lens object side surface.

In the case of |DL1/RL1$a$|=0.4, a ratio of a convex surface height (or a concave surface depth) to the outer diameter DL1 is 5.05%. Assuming a small-diameter endoscope with DL1 at Ø2 mm, the convex surface height (or a concave surface depth) is 0.1 mm, and a protrusion (dent) amount from the lens outer diameter end is sufficiently small.

In the case of a convex surface, a protruding amount like this is a level at which a structure of avoiding lens breakage or incidence of illumination light which is the problem of PTL 2 and PTL 3 can be provided. In the case of a concave surface, with a dent amount like this, remaining stains in cleaning of a lens surface or an increase in a reflection loss caused by Fresnel reflection in the concave surface peripheral portion does not have to be worried about.

If |DL1/RL1$a$| becomes larger than 0.4 on the convex surface, protrusion from the lens outer diameter end becomes too large and a machine design for avoiding the lens breakage or incidence of illumination light becomes difficult, which is not desirable. If |DL1/RL1$a$| becomes larger than 0.4 on the concave surface, dent from the lens outer diameter end becomes too large and deterioration in cleaning performances or an increase in Fresnel reflection rate in the concave surface peripheral portion is caused, which is not desirable.

The endoscope objective optical system more preferably satisfies the following expression (4):

$$-3<fL1/ft<-1 \quad (4)$$

where fL1 is a focal distance of the first lens.

The expression (4) is a condition relating to the focal distance of the first lens. In order to make Iw larger than Ia in relation with the expression (2), not only that power of the first lens needs to be negative but also an absolute amount of the power has an appropriate range. If fL1/ft is smaller than −3, the power is too weak and angle widening in the water becomes difficult, which is not desirable. If fL1/ft is larger than −1, the negative power is so strong that an excessive correction tendency of field curvature is caused, which is not preferable.

By constituting the first lens by the plano-concave lens with the planar object side surface, the objective optical system with favorable workability and a low cost can be provided. In order to have the negative power as the entire first lens, the image side surface is a concave surface, but any one of the plane, the convex surface, and the concave surface can be employed for the object side surface. However, since the plane is the most preferable from the viewpoint of workability, constituting the first lens by the plano-concave lens is the most preferable from the viewpoint of workability and a cost. Moreover, by constituting the first lens by the plano-concave lens, a highly hard and hardly workable material such as sapphire with poor workability can be employed, which contributes to improvement of abrasion resistance and the like.

In the aforementioned embodiment, the constitution in which the front group GF includes the first lens group and the second lens group is described, but this is not limiting, and such a constitution not including the second lens group can be employed, for example. Moreover, the example in which a single lens is applied to the second lens group is described, but a cemented lens can be also applied. If the front group GF has the second lens group, the aforementioned expression (2) is satisfied with allowance.

That is, as described in this embodiment, in order to realize angle widening and sufficient correction of field curvature in the underwater observation, a so-called retro-focus type composed of the negative front group-positive back group by sandwiching the brightness diaphragm is preferably applied. Moreover, since it is difficult to bear the negative refractive power of the front group only by one group depending on the underwater view angle, it is preferably divided into the two negative groups, that is, the first group and the second group. Moreover, the first lens group is preferably constituted by a single lens which can be thinned as described above, and for the second lens group, since an angle is relaxed by refraction in the first lens group and the light beam height is lowered, the single lens and the cemented lens can be both applied.

By constituting so as to satisfy the conditions of the aforementioned expression (1) as above, sufficient angle widening can be realized even in the underwater observation. Moreover, in the constitution having the second lens group by dividing the front group GF into two negative groups, that is, the first lens group and the second lens group, the aforementioned expression (2) is satisfied with allowance.

Figure 2A:
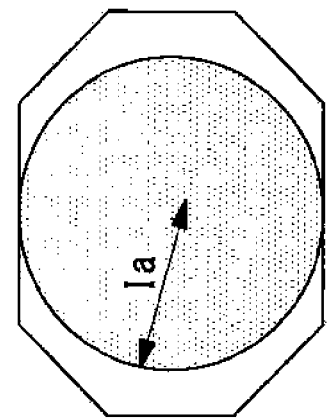

FIG. 2 are conceptual diagrams illustrating image pickup ranges of the underwater observation and the observation in the air and intuitively illustrate that the effective image pickup area in the state of observation in the air is narrower than that in the underwater observation state as described above. FIG. 2A illustrates an image pickup area on a solid image pickup device in the underwater observation state and on a premise that an electrical view-field mask having an octagonal shape is placed, it shows that the entire effective image pickup area in a hatched octagonal mask can be utilized, and the maximum image height in the octagonal mask is Iw.

Figure 2B:
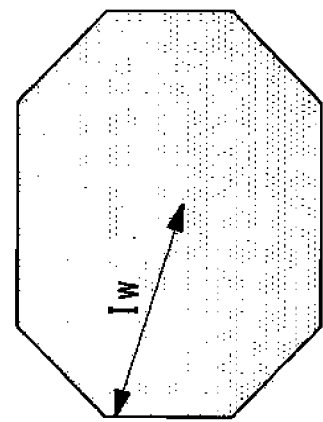

FIG. 2B illustrates an image pickup area on the solid image pickup device in the state of observation in the air, and a hatched inside of a circle with a radius Ia is an image pickup area in the state of observation in the air, and a non-hatched region sandwiched between the octagonal mask and the circle is an optically invalid region on which an image of an object is not formed. By allowing presence of the optically invalid region in the observation in the air as described above, wide-angle underwater observation is made possible even if the object side surface of the first lens is planar.

The structure in which the object side surface of the first lens is planar is general as a structure of an endoscope tip end, and no special devise is needed for direct light incident flare from an illumination system, not shown in FIG. 1. The planar structure without protrusion does not increase a probability of damage on the first lens caused by a collision of an article from the object side. Moreover, despite the view angle which could be classified as a fish-eye lens in general, the outer diameter DL1 of the first lens is as extremely small as Ø2.2 mm and does not apply a burden to the structural design of the endoscope tip end.

Sapphire with high hardness is assumed for the material of the first lens, and a product also with excellent mechanical durability as a material characteristic can be provided. Moreover, by performing metallization on an outer periphery of the sapphire and soldering it to a frame, a mirror frame structure with extremely high reliability can be provided.

A material with a high refractive index is used for the plano-concave lens of the second group in order to prevent excessive correction of field curvature which can easily become excessive correction by a negative refractive power made stronger with angle-widening to a super-wide angle. Moreover, by using a material with a high refractive index also for the concave lens of the cemented lens of the back group, excessive correction of field curvature is similarly prevented.

As described above, according to this embodiment, a view angle is wide in the underwater observation, and mounting design can be made easily while reliability as a medical endoscope is ensured.

EXAMPLE

Subsequently, Examples 1 to 9 of the endoscope objective optical system according to the aforementioned embodiment will be described by referring to FIGS. 3 to 29. In lens data described in each Example, reference character r denotes a radius of curvature (unit: mm), reference character d denotes a surface interval (mm), reference character Nd denotes a refractive index to the d line, and reference character Vd denotes the Abbe number to the d line.

Example 1

Figure 3:
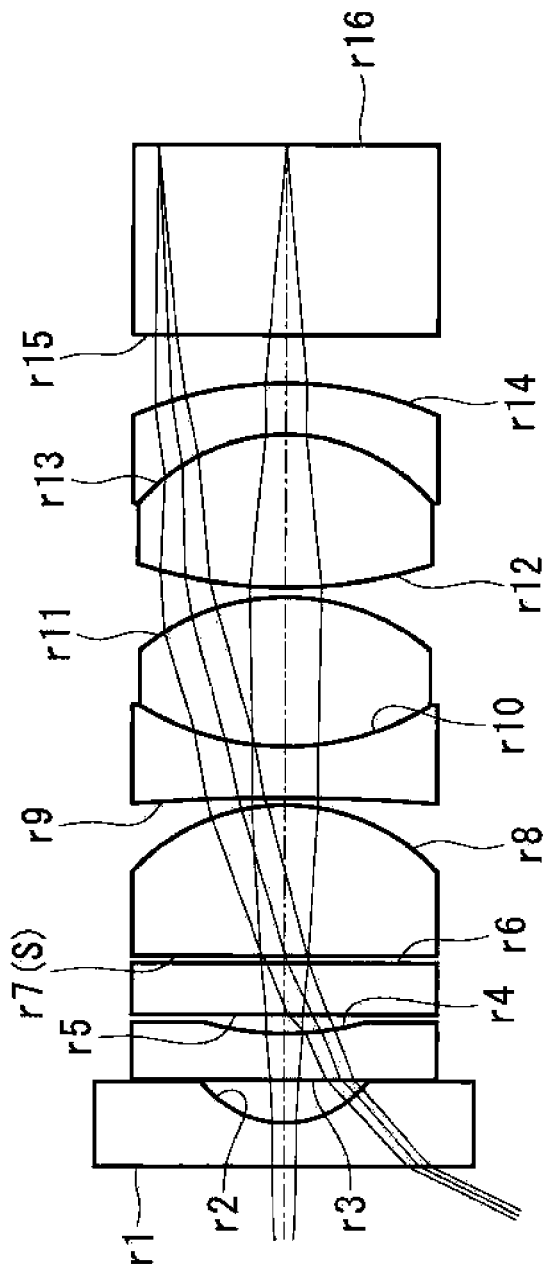
FIG. 3 is a sectional view illustrating the entire constitution of the endoscope objective optical system according to a first example of the present invention.
Figure 5:
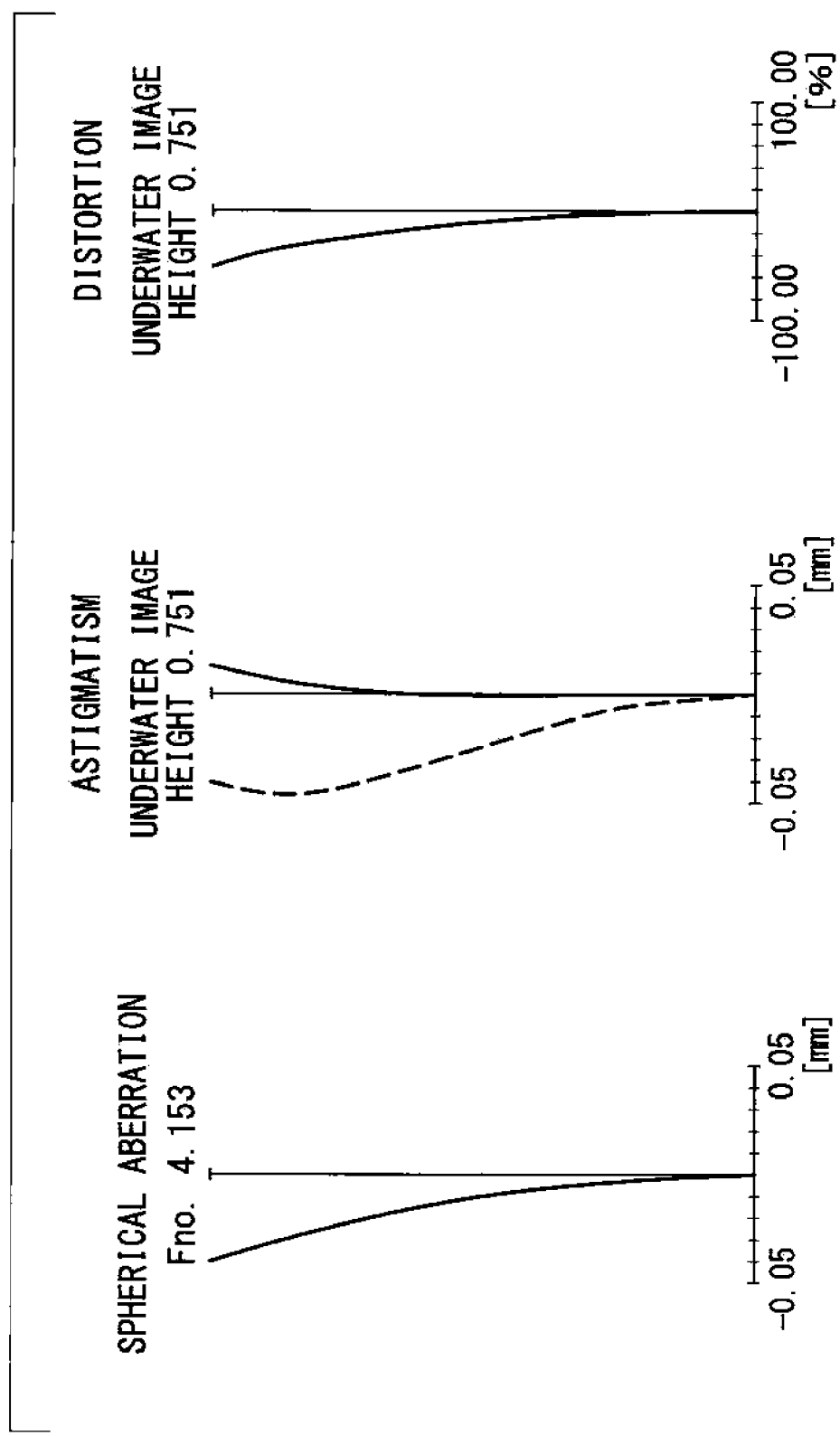
FIG. 5 is an aberration diagram of the state of the underwater observation of the endoscope objective optical system according to the first example of the present invention.

A lens constitution of the endoscope objective optical system according to Example 1 of the present invention is illustrated in FIGS. 3 and 4. FIG. 4A illustrates an underwater observation state and FIG. 4B illustrates a state of observation in the air. An aberration diagram of the underwater observation state is shown in FIG. 5.

The endoscope objective optical system of Example 1 is composed of a first group composed of a plano-concave lens (first lens), a second group composed of a plano-concave lens, a color correction filter, a brightness diaphragm assuming mounting on a thin plate, and a back group having a positive refractive power in order from the object side. The back group is composed of three groups, and all of them have the positive refractive power. It is assumed that an image pickup surface of a solid image pickup device is arranged on an image plane.

An image height Iw in the underwater observation state in FIG. 4A is 0.7510 mm, and this image height is assumed to match an effective image pickup area of the solid image pickup device, and the entire effective image pickup area of the solid image pickup device is used in the underwater observation state. The underwater view angle at this time is 129.4° and is an extremely wide angle for the underwater observation, and an object in the water can be observed by using the entire effective image pickup area of the solid image pickup device.

In the observation state in the air in FIG. 4B, since the first lens is planar, only a light beam up to a view angle in the air at 180° can enter the lens. A principal ray incident substantially in parallel with the plane of the first lens forms an image at a position lower than Iw on the image plane, Ia corresponding to the maximum image height in the air is 0.5995 mm, and a relation of Ia/Iw at 0.798 is obtained. As a result, in the state of observation in the air, an image partially using the effective image pickup are of the solid image pickup device is obtained.

Image pickup ranges of the underwater observation and the observation in the air are states as illustrated in FIG. 2.

The lens data of the endoscope objective optical system according to Example 1 is shown below.

Lens Data

| Plane number | r | d | Nd | Vd |
|---|---|---|---|---|
| 1 | ∞ | 0.25 | 1.76820 | 71.79 |
| 2 | 0.639 | 0.27 | | |
| 3 | ∞ | 0.25 | 2.00330 | 28.27 |
| 4 | 1.961 | 0.11 | | |
| 5 | ∞ | 0.30 | 1.52134 | 74.98 |
| 6 | ∞ | 0.03 | | |
| 7 (STO) | ∞ | 0.87 | 2.00330 | 28.27 |
| 8 | −1.243 | 0.05 | | |
| 9 | −9.813 | 0.30 | 2.00330 | 28.27 |
| 10 | 1.717 | 0.86 | 1.72916 | 54.68 |
| 11 | −1.345 | 0.05 | | |
| 12 | 2.838 | 0.87 | 1.48749 | 70.23 |
| 13 | −1.108 | 0.30 | 1.92286 | 18.90 |
| 14 | −2.439 | 0.28 | | |
| 15 | ∞ | 1.10 | 1.51633 | 64.14 |
| 16 (image plane) | ∞ | | | |

Example 2

Figure 6:
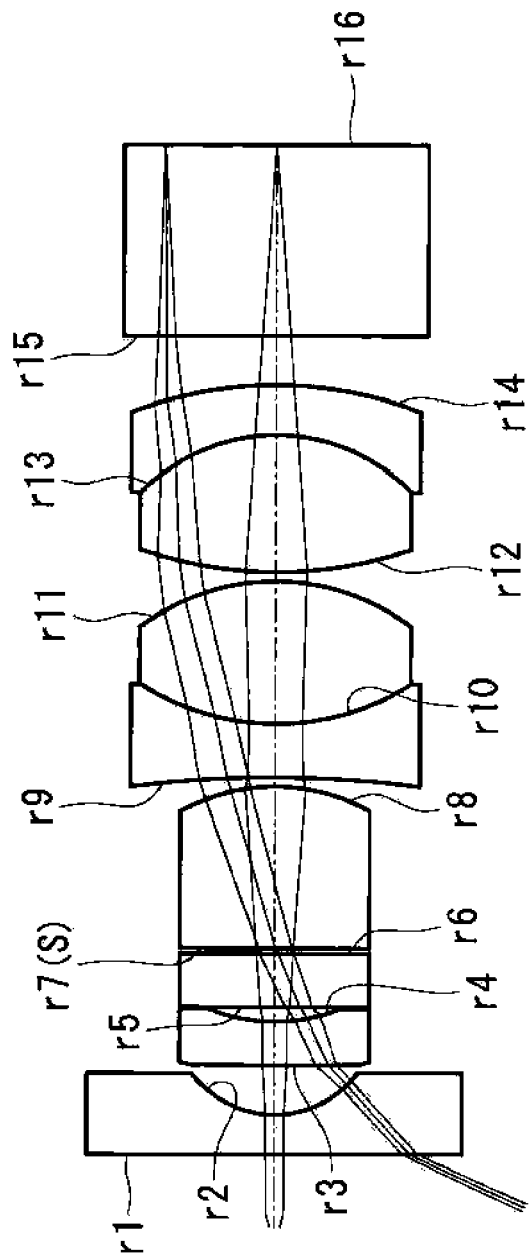
FIG. 6 is a sectional view illustrating the entire constitution of the endoscope objective optical system according to a second example of the present invention.
Figure 8:
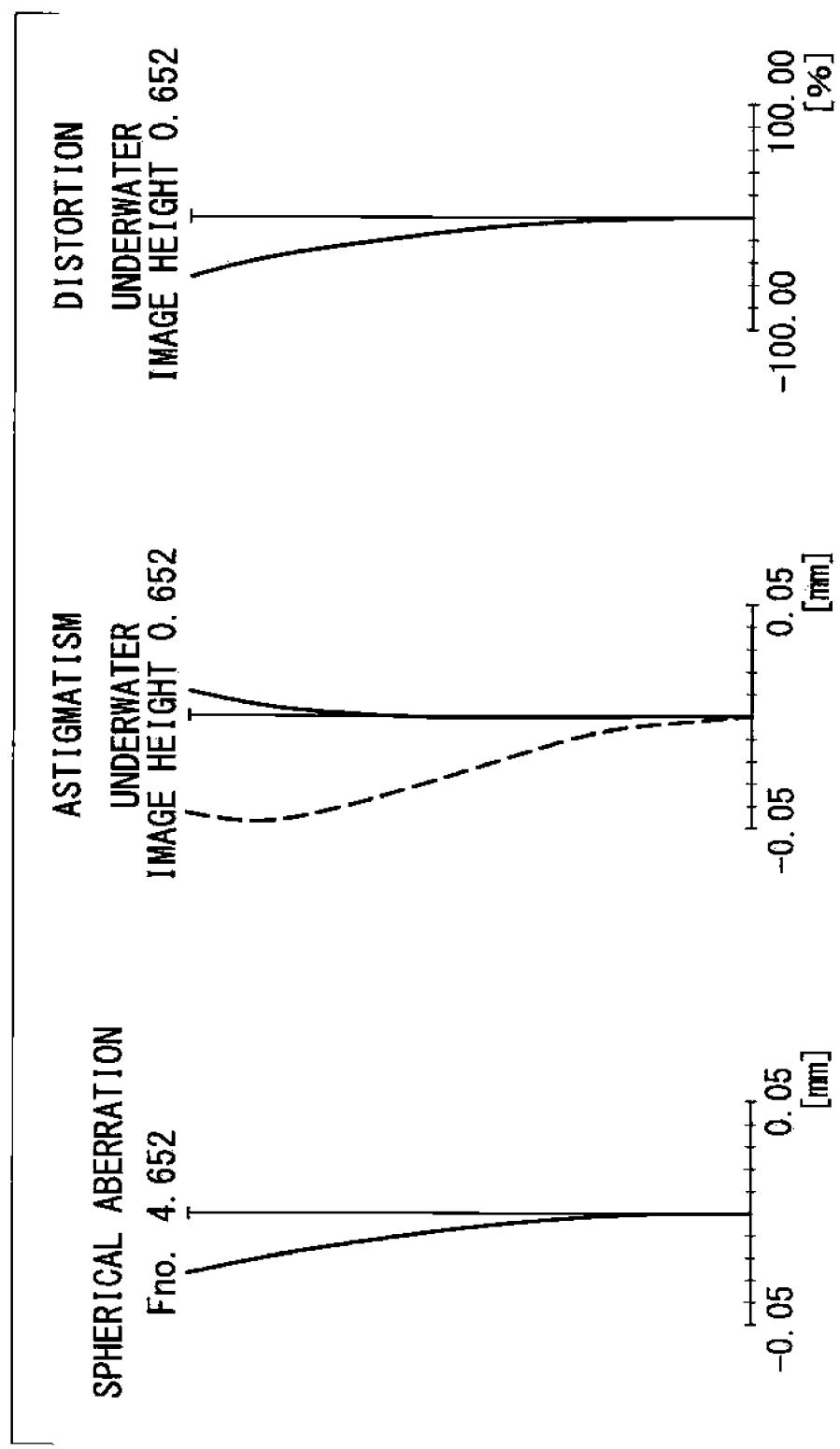
FIG. 8 is an aberration diagram of the state of the underwater observation of the endoscope objective optical system according to the second example of the present invention.

A lens constitution of the endoscope objective optical system according to Example 1 of the present invention is illustrated in FIGS. 6 and 7. FIG. 7A illustrates an underwater observation state and FIG. 7B illustrates a state of observation in the air. An aberration diagram of the underwater observation state is shown in FIG. 8.

The endoscope objective optical system of Example 2 is composed of a first group composed of a plano-concave lens (first lens), a second group composed of a concave meniscus lens, a color correction filter, a brightness diaphragm, and a back group having a positive refractive power in order from the object side. The back group is composed of three groups, and all of them have the positive refractive power similarly to Example 1.

A combination with a solid image pickup device with a size smaller than that of Example 1 is assumed, and an image height Iw in the underwater observation state is 0.6520 mm. With Ia at 0.5195 mm, Ia/Iw at 0.797, and the underwater view angle at 129.8°, the specification similar to that of Example 1 was realized even though the size of the solid image pickup device is different, and the image pickup ranges of the underwater observation and the observation in the air are states as shown in FIG. 2 similarly to Example 1.

The lens data of the endoscope objective optical system according to Example 2 is shown below.
Lens Data

| Plane number | r | d | Nd | Vd |
|---|---|---|---|---|
| 1 | ∞ | 0.25 | 1.76820 | 71.79 |
| 2 | 0.639 | 0.27 | | |
| 3 | 9.789 | 0.25 | 2.00330 | 28.27 |
| 4 | 1.243 | 0.10 | | |
| 5 | ∞ | 0.30 | 1.52134 | 74.98 |
| 6 | ∞ | 0.03 | | |
| 7 (STO) | ∞ | 0.93 | 2.00330 | 28.27 |
| 8 | −1.132 | 0.05 | | |
| 9 | −7.331 | 0.30 | 2.00330 | 28.27 |
| 10 | 1.485 | 0.83 | 1.72916 | 54.68 |
| 11 | −1.354 | 0.05 | | |
| 12 | 2.621 | 0.78 | 1.51633 | 64.14 |
| 13 | −1.161 | 0.30 | 1.92286 | 18.90 |
| 14 | −2.417 | 0.29 | | |
| 15 | ∞ | 1.10 | 1.51633 | 64.14 |
| 16 (image plane) | ∞ | | | |

Example 3

Figure 9:
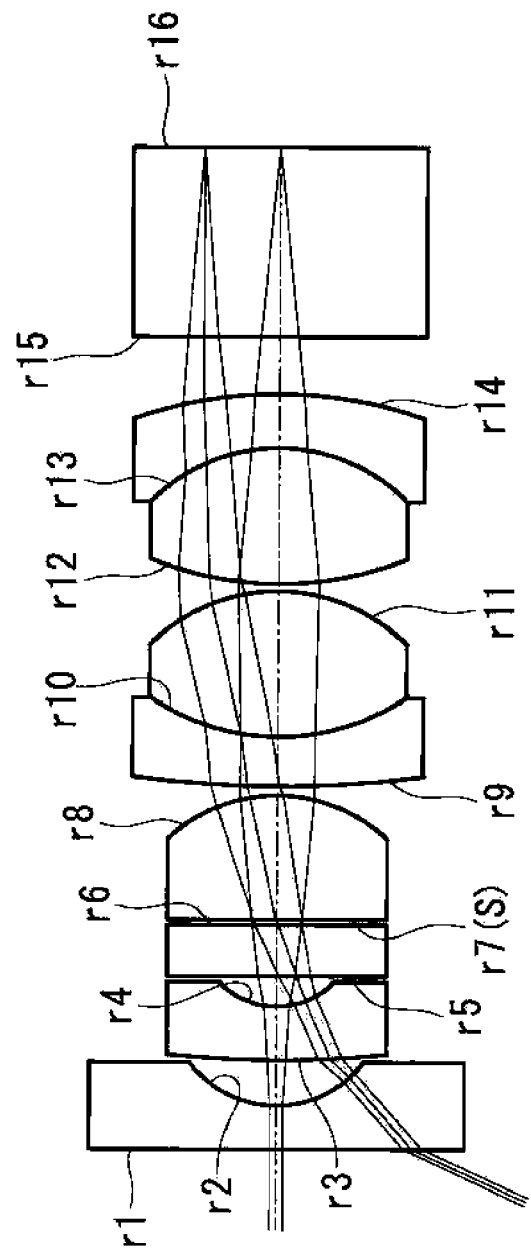
FIG. 9 is a sectional view illustrating the entire constitution of the endoscope objective optical system according to a third example of the present invention.

A lens constitution of the endoscope objective optical system according to Example 3 of the present invention is illustrated in FIGS. 9 and 10. FIG. 10A illustrates an underwater observation state and FIG. 10B illustrates a state of observation in the air. An aberration diagram of the underwater observation state is shown in FIG. 11.

The endoscope objective optical system of Example 3 is composed of a first group composed of a plano-concave lens (first lens), a second group composed of a concave meniscus lens, a color correction filter, a brightness diaphragm, and a back group having a positive refractive power in order from the object side. The back group is composed of three groups, and all of them have the positive refractive power. A combination with a solid image pickup device with a size further smaller than that of Example 2 is assumed, and an image height Iw in the underwater observation state is 0.4480 mm. With Ia at 0.3585 mm, Ia/Iw at 0.800, and the underwater view angle at 129.6°, the specification similar to that of Examples 1 and 2 can be realized even if the size of the solid image pickup device is further smaller.

The lens data of the endoscope objective optical system according to Example 3 is shown below.
Lens Data

| Plane number | r | d | Nd | Vd |
|---|---|---|---|---|
| 1 | ∞ | 0.25 | 1.76820 | 71.79 |
| 2 | 0.639 | 0.27 | | |
| 3 | 9.406 | 0.30 | 1.88300 | 40.76 |
| 4 | 0.462 | 0.17 | | |
| 5 | ∞ | 0.30 | 1.52134 | 74.98 |
| 6 | ∞ | 0.03 | | |
| 7 (STO) | ∞ | 0.71 | 1.80100 | 34.97 |
| 8 | −0.915 | 0.05 | | |
| 9 | 6.526 | 0.30 | 2.00330 | 28.27 |
| 10 | 1.354 | 0.83 | 1.51742 | 52.43 |
| 11 | −1.108 | 0.05 | | |
| 12 | 1.988 | 0.79 | 1.58913 | 61.14 |
| 13 | −1.041 | 0.30 | 1.92286 | 18.90 |
| 14 | −2.551 | 0.33 | | |
| 15 | ∞ | 1.10 | 1.51633 | 64.14 |
| 16 (image plane) | ∞ | | | |

Example 4

Figure 12:
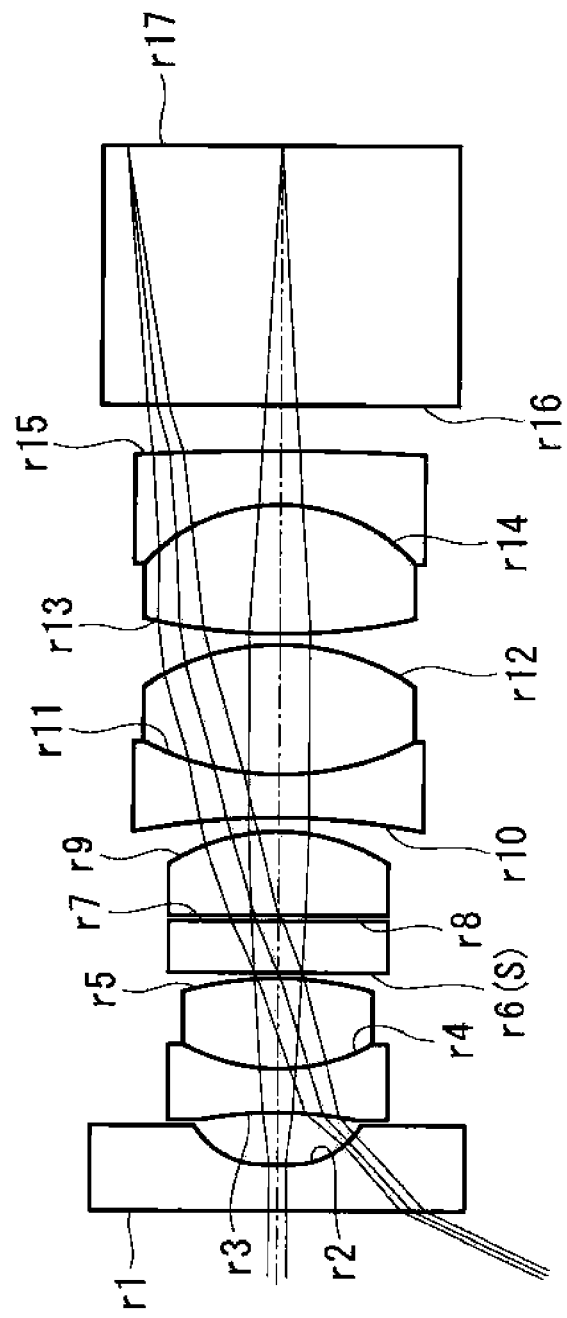
FIG. 12 is a sectional view illustrating the entire constitution of the endoscope objective optical system according to a fourth example of the present invention.
Figure 14:
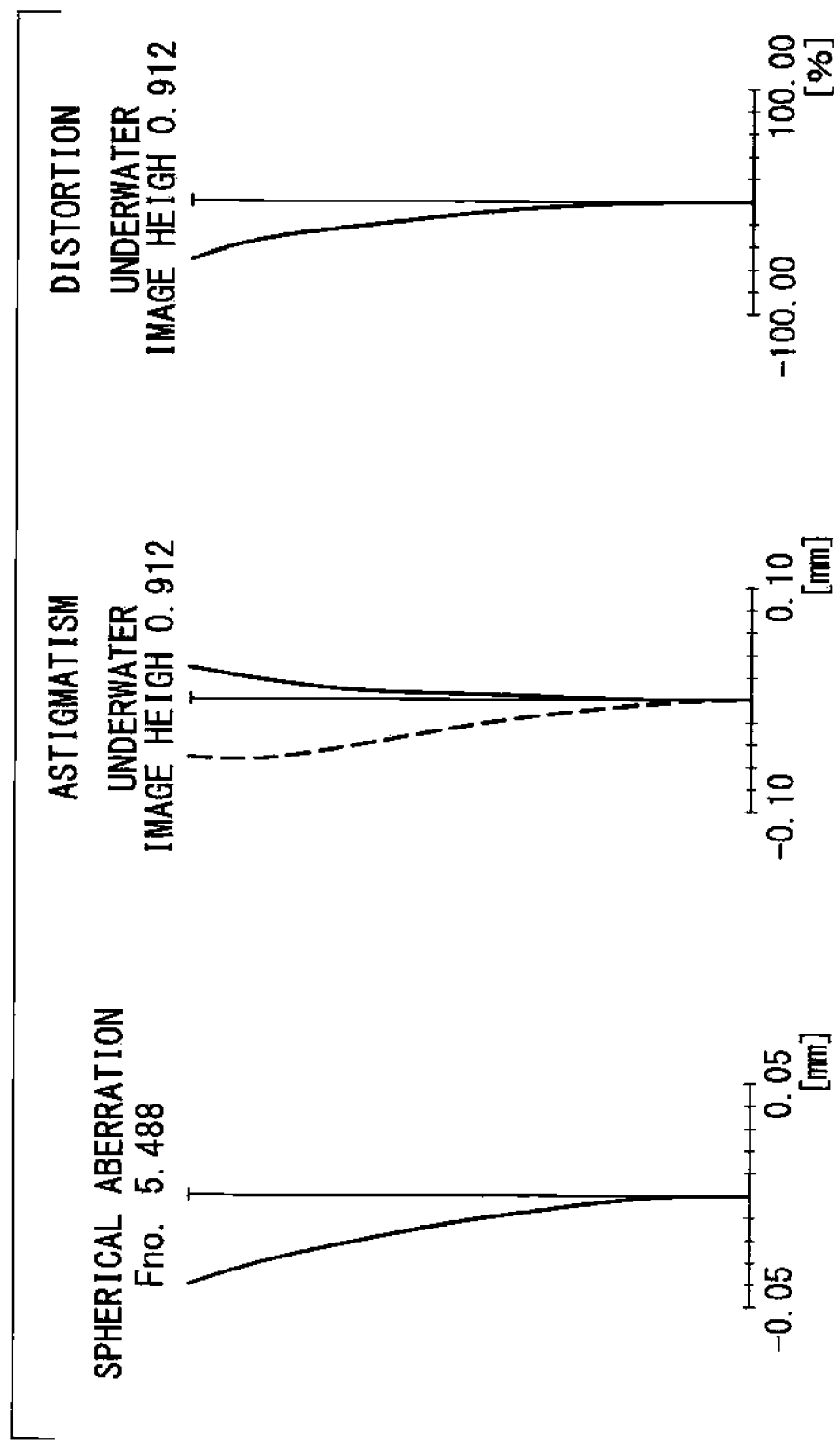
FIG. 14 is an aberration diagram of the state of the underwater observation of the endoscope objective optical system according to the fourth example of the present invention.

A lens constitution of the endoscope objective optical system according to Example 4 of the present invention is illustrated in FIGS. 12 and 13. FIG. 13A illustrates an underwater observation state and FIG. 13B illustrates a state of observation in the air. An aberration diagram of the underwater observation state is shown in FIG. 14.

The endoscope objective optical system of Example 4 is composed of a first group composed of a plano-concave lens (first lens), a second group composed of a negative cemented lens, a color correction filter, a brightness diaphragm, and a back group having a positive refractive power in order from the object side. The back group is composed of three groups, and all of them have the positive refractive power. A combination with a solid image pickup device with a size larger than that of Example 1 is assumed, and an image height Iw in the underwater observation state is 0.9120 mm. With Ia at 0.7301 mm, Ia/Iw at 0.801, and the underwater view angle at 129.8°, the specification similar to that of Examples 1 to 3 can be realized even if the size of the solid image pickup device is larger. Higher pixels can be realized by a larger solid image pickup device, and in order to make aberration correction according to that, the second group is constituted by a cemented lens so as to improve the aberration correction capability.

A sapphire plano-concave lens having the same outer diameter and shape is used for the first lens of Examples 1 to 4 having substantially the same underwater view angle. In the case of a super-wide angle lens as in this embodiment, a maximum outer diameter of an optical system tends to be determined by the outer diameter of the first lens with a light beam height higher than the size of the solid image pickup device, and there is freedom in selection relating to the size of the solid image pickup device.

Since a field depth can be easily ensured by a super-wide angle, the larger solid image pickup device is desirable since the number of pixels or a dynamic range can be improved, but if it is too large, the solid image pickup device side affects the outer diameter of the endoscope tip end. Thus, the relationship between the underwater image height Iw and the outer diameter DL1 of the first lens reflecting the size of the solid image pickup device is preferably set so as to satisfy the following expression (8).

$$0.2 < Iw/DL1 < 0.5 \quad (8)$$

If Iw/DL1 is 0.2 or less, the number of pixels or the dynamic range tends to be insufficient, and the setting is not preferable from the viewpoint of an image quality. If Iw/DL1 is 0.5 or more, the solid image pickup device side makes a limitation factor of the tip end outer diameter, and it also means that DL1 is unnecessarily small, and the balance is not good for the endoscope tip end design.

The lens data of the endoscope objective optical system according to Example 4 is shown below.

Lens Data

| Plane number | r | d | Nd | Vd |
|---|---|---|---|---|
| 1 | ∞ | 0.25 | 1.76820 | 71.79 |
| 2 | 0.639 | 0.33 | | |
| 3 | −2.582 | 0.25 | 2.00330 | 28.27 |
| 4 | 1.108 | 0.51 | 1.80100 | 34.97 |
| 5 | −2.461 | 0.03 | | |
| 6 (STO) | ∞ | 0.30 | 1.52134 | 74.98 |
| 7 | ∞ | 0.03 | | |
| 8 | ∞ | 0.48 | 2.00330 | 28.27 |
| 9 | −1.345 | 0.10 | | |
| 10 | −4.079 | 0.25 | 2.00330 | 28.27 |
| 11 | 1.891 | 0.75 | 1.72916 | 54.68 |
| 12 | −1.354 | 0.05 | | |
| 13 | 3.473 | 0.75 | 1.72916 | 54.68 |
| 14 | −1.132 | 0.30 | 2.00330 | 28.27 |
| 15 | −17.115 | 0.28 | | |
| 16 | ∞ | 1.50 | 1.51633 | 64.14 |
| 17 (image plane) | ∞ | | | |

Example 5

Figure 15:
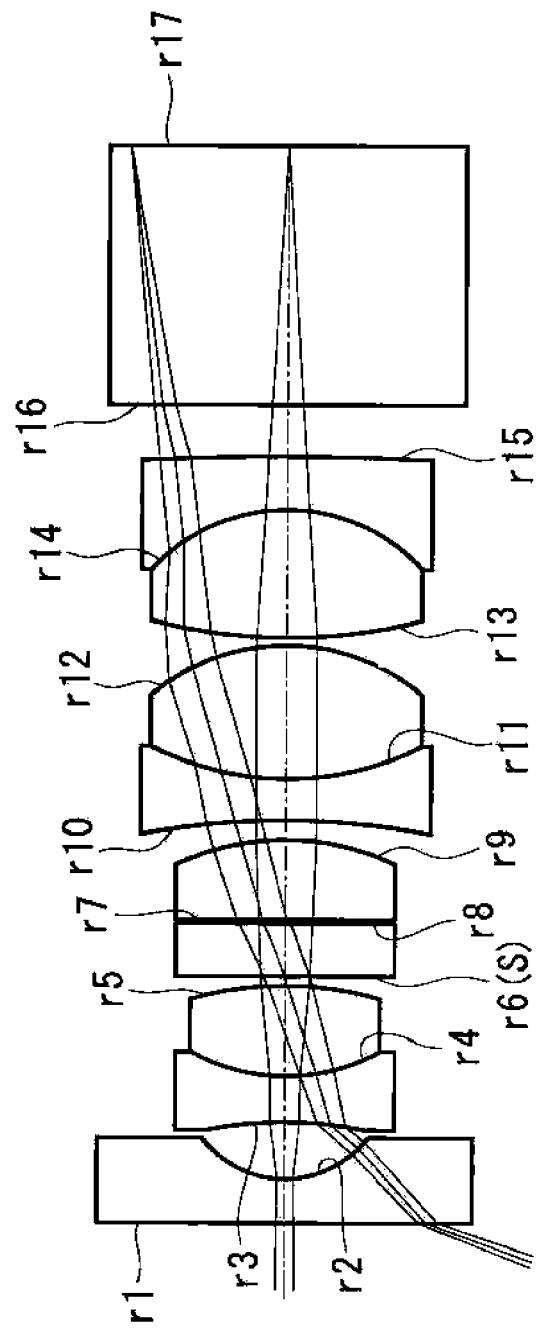
FIG. 15 is a sectional view illustrating the entire constitution of the endoscope objective optical system according to a fifth example of the present invention.
Figure 17:
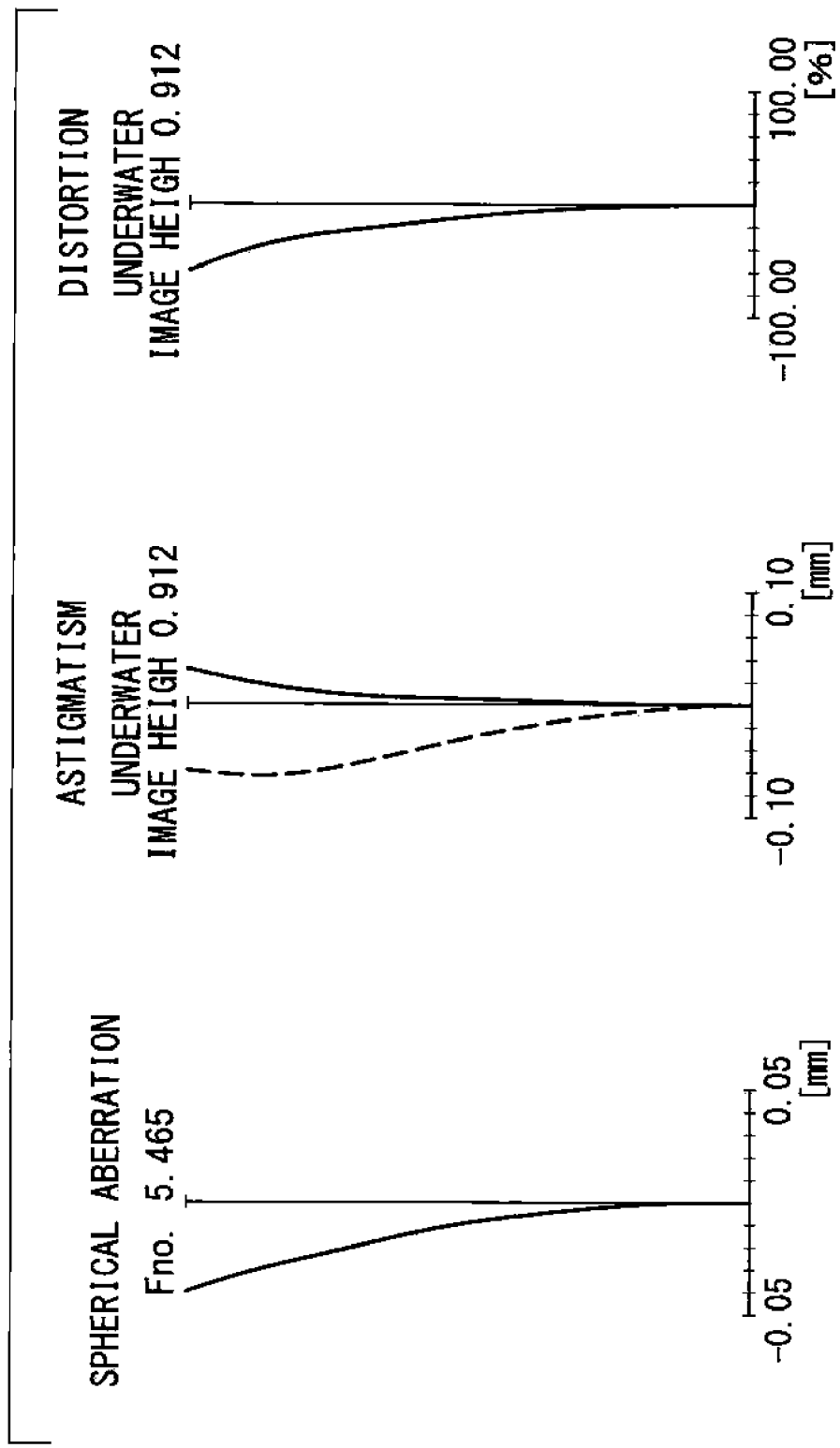
FIG. 17 is an aberration diagram of the state of the underwater observation of the endoscope objective optical system according to the fifth example of the present invention.

A lens constitution of the endoscope objective optical system according to Example 5 of the present invention is illustrated in FIGS. 15 and 16. FIG. 16A illustrates an underwater observation state and FIG. 16B illustrates a state of observation in the air. An aberration diagram of the underwater observation state is shown in FIG. 17.

The endoscope objective optical system of Example 5 assumes a solid image pickup device with the same size as that of Example 4 and has an underwater view angle wider than that in Example 4, the underwater view angle being 139.8°. The endoscope objective optical system in Example 5 is composed of a first group composed of a plano-concave lens (first lens), a second group composed of a negative cemented lens, a color correction filter, a brightness diaphragm, and a back group having a positive refractive power in order from the object side. The back group is composed of three groups, and all of them have the positive refractive power. An image height Iw in the underwater observation state is 0.9120 mm. With Ia at 0.7019 mm and Ia/Iw at 0.770, and since Ia is smaller with reduction of the focal distance ft with angle-widening, Ia/Iw is smaller than Example 4.

The lens data of the endoscope objective optical system according to Example 5 is shown below.

Lens Data

| Plane number | r | d | Nd | Vd |
|---|---|---|---|---|
| 1 | ∞ | 0.25 | 1.76820 | 71.79 |
| 2 | 0.639 | 0.33 | | |
| 3 | −2.211 | 0.25 | 2.00330 | 28.27 |
| 4 | 1.108 | 0.54 | 1.80100 | 34.97 |
| 5 | −2.280 | 0.03 | | |
| 6 (STO) | ∞ | 0.30 | 1.52134 | 74.98 |
| 7 | ∞ | 0.03 | | |
| 8 | ∞ | 0.48 | 2.00330 | 28.27 |
| 9 | −1.425 | 0.10 | | |
| 10 | −4.288 | 0.25 | 2.00330 | 28.27 |
| 11 | 1.869 | 0.75 | 1.72916 | 54.68 |
| 12 | −1.298 | 0.05 | | |
| 13 | 3.423 | 0.75 | 1.72916 | 54.68 |
| 14 | −1.108 | 0.30 | 2.00330 | 28.27 |
| 15 | −19.376 | 0.29 | | |
| 16 | ∞ | 1.50 | 1.51633 | 64.14 |
| 17 (image plane) | ∞ | | | |

Example 6

Figure 18:
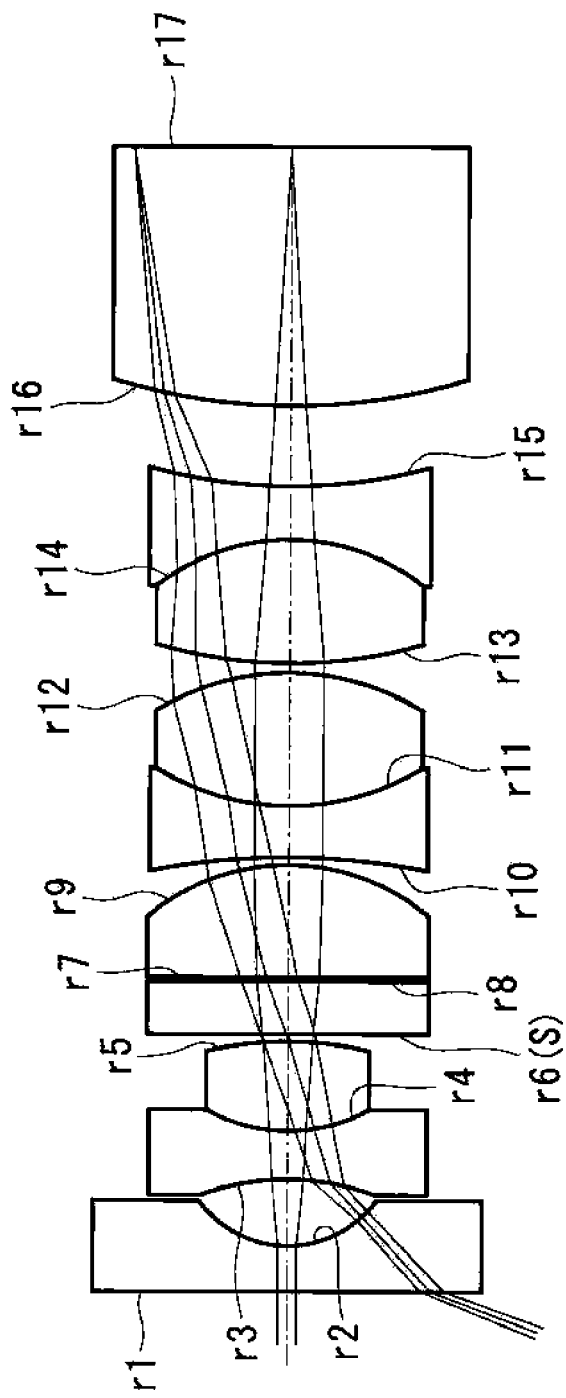
FIG. 18 is a sectional view illustrating the entire constitution of the endoscope objective optical system according to a sixth example of the present invention.
Figure 20:
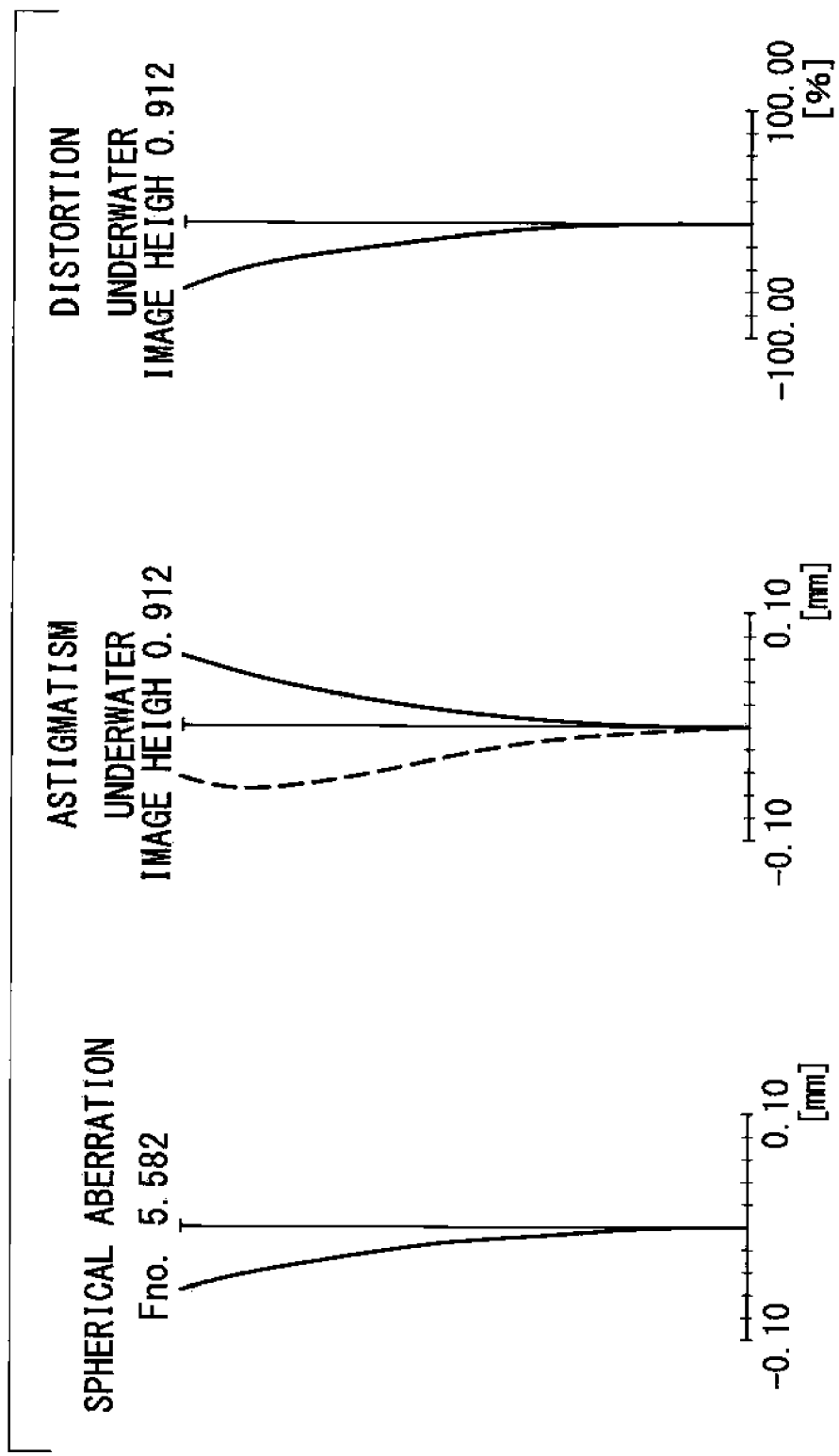
FIG. 20 is an aberration diagram of the state of the underwater observation of the endoscope objective optical system according to the sixth example of the present invention.

A lens constitution of the endoscope objective optical system according to Example 6 of the present invention is illustrated in FIGS. 18 and 19. FIG. 19A illustrates an underwater observation state and FIG. 19B illustrates a state of observation in the air. An aberration diagram of the underwater observation state is shown in FIG. 20.

The endoscope objective optical system of Example 6 has substantially the same optical specification as that of Example 5 but is different in a point that it has a convex lens for exit pupil adjustment at a spot closest to the image plane. The endoscope objective optical system of Example 6 is composed of a first group composed of a plano-concave lens (first lens), a second group composed of a negative cemented lens, a color correction filter, a brightness diaphragm, and a back group having a positive refractive power in order from the object side. The back group is composed of four groups and has refractive powers of positive-positive-negative-positive in order from the brightness diaphragm side.

The lens data of the endoscope objective optical system according to Example 6 is shown below.

Lens Data

| Plane number | r | d | Nd | Vd |
|---|---|---|---|---|
| 1 | ∞ | 0.25 | 1.76820 | 71.79 |
| 2 | 0.639 | 0.39 | | |
| 3 | −1.581 | 0.28 | 2.00330 | 28.27 |
| 4 | 0.942 | 0.52 | 1.80100 | 34.97 |
| 5 | −1.800 | 0.03 | | |
| 6 (STO) | ∞ | 0.30 | 1.52100 | 65.13 |
| 7 | ∞ | 0.03 | | |
| 8 | ∞ | 0.65 | 2.00330 | 28.27 |
| 9 | −1.381 | 0.05 | | |
| 10 | −4.502 | 0.30 | 2.00330 | 28.27 |
| 11 | 1.535 | 0.77 | 1.78800 | 47.37 |
| 12 | −1.535 | 0.05 | | |
| 13 | 2.920 | 0.72 | 1.72916 | 54.68 |
| 14 | −1.243 | 0.30 | 2.00330 | 28.27 |
| 15 | 3.602 | 0.45 | | |
| 16 | 3.254 | 1.50 | 1.51633 | 64.14 |
| 17 (image plane) | ∞ | | | |

Example 7

Figure 21:
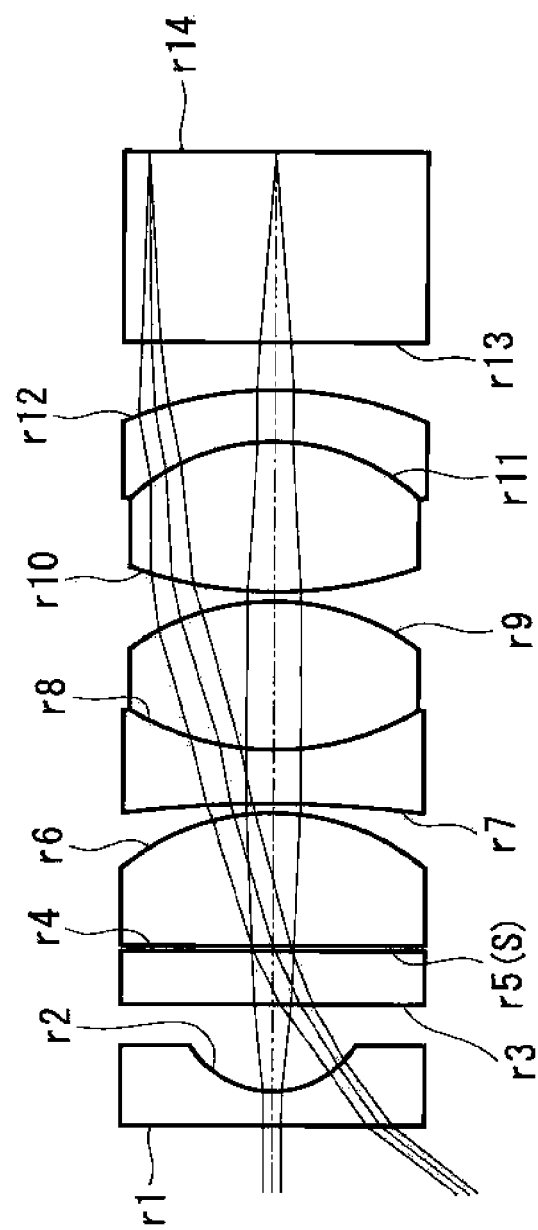
FIG. 21 is a sectional view illustrating the entire constitution of the endoscope objective optical system according to a seventh example of the present invention.
Figure 23:
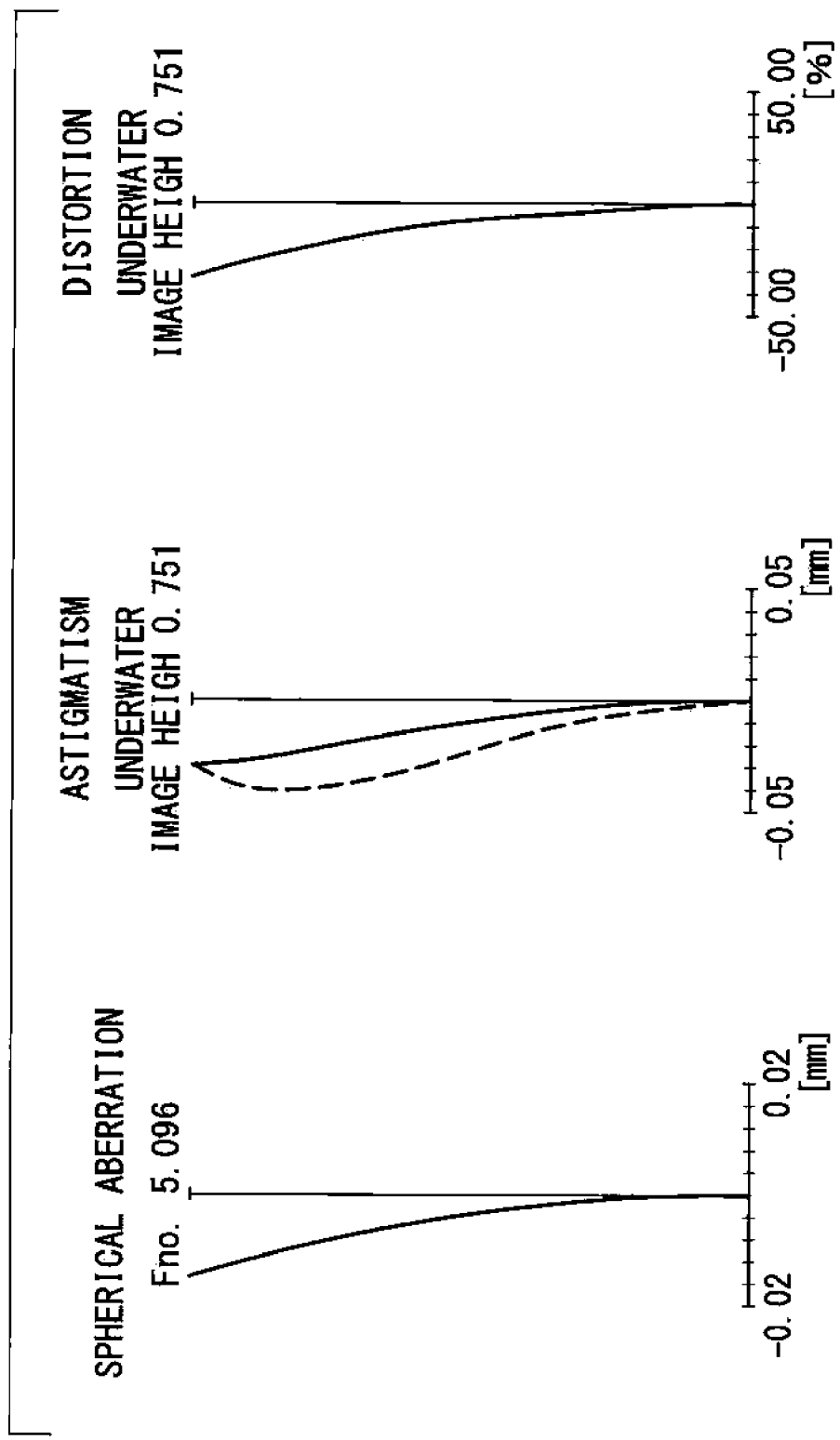
FIG. 23 is an aberration diagram of the state of the underwater observation of the endoscope objective optical system according to the seventh example of the present invention.

A lens constitution of the endoscope objective optical system according to Example 7 of the present invention is illustrated in FIGS. 21 and 22. FIG. 22A illustrates an underwater observation state and FIG. 22B illustrates a state of observation in the air. An aberration diagram of the underwater observation state is shown in FIG. 23.

In the endoscope objective optical system of Example 7, the underwater image height Iw is substantially the same as that of Example 1 but the underwater view angle is kept as low as at 105.0°, and the front group is composed of only one negative group. With this degree of the underwater view angle, the front group can be constituted only by one negative group. The endoscope objective optical system in Example 7 is composed of a first group composed of a plano-concave lens (first lens), a color correction filter, a brightness diaphragm, and a back group having a positive refractive power in order from the object side. The back group is composed of three groups, and all of them have the positive refractive power. With Ia/Iw at 0.937, which is the largest in Examples of the present invention, while the outer diameter DL1 of the first lens is the smaller than any other Examples having substantially the same underwater image height Iw. Thus, this Example is suitable when an angle is to be widened in the water with an endoscope with a smaller diameter.

The lens data of the endoscope objective optical system according to Example 7 is shown below.
Lens Data

| Plane number | r | d | Nd | Vd |
|---|---|---|---|---|
| 1 | ∞ | 0.20 | 1.76820 | 71.79 |
| 2 | 0.614 | 0.50 | | |
| 3 | ∞ | 0.30 | 1.52134 | 74.98 |
| 4 | ∞ | 0.03 | | |
| 5 (STO) | ∞ | 0.78 | 2.00330 | 28.27 |
| 6 | −1.392 | 0.05 | | |
| 7 | −7.408 | 0.30 | 2.00330 | 28.27 |
| 8 | 1.641 | 0.86 | 1.72916 | 54.68 |
| 9 | −1.502 | 0.05 | | |
| 10 | 2.461 | 0.87 | 1.48749 | 70.23 |
| 11 | −1.243 | 0.30 | 1.92286 | 18.90 |
| 12 | −2.132 | 0.27 | | |
| 13 | ∞ | 1.10 | 1.51633 | 64.14 |
| 14 (image plane) | ∞ | | | |

Example 8

Figure 24:
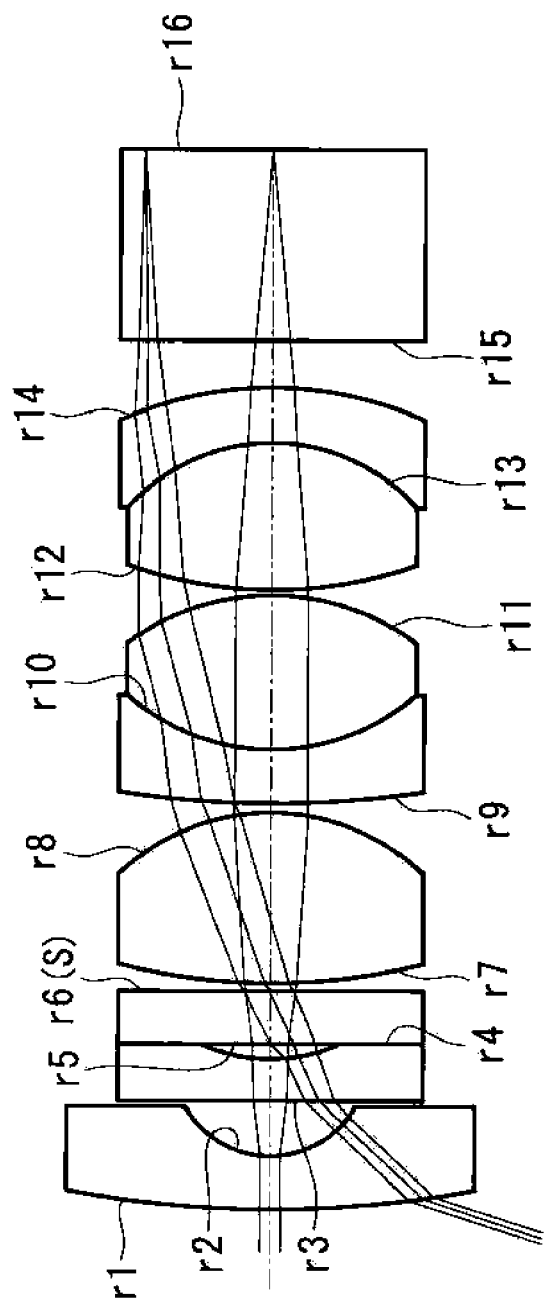
FIG. 24 is a sectional view illustrating the entire constitution of the endoscope objective optical system according to an eighth example of the present invention.
Figure 26:
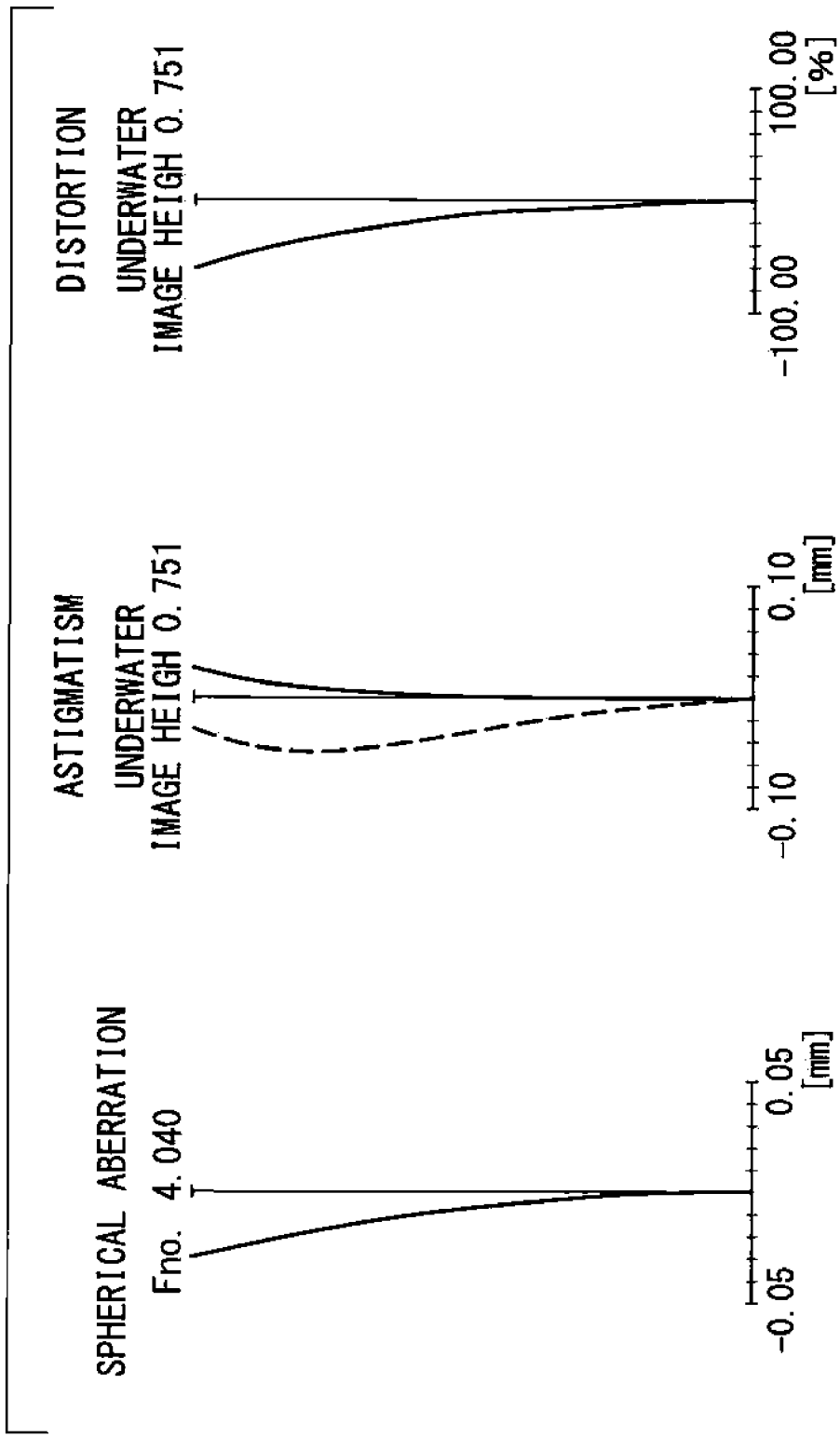
FIG. 26 is an aberration diagram of the state of the underwater observation of the endoscope objective optical system according to the eighth example of the present invention.

A lens constitution of the endoscope objective optical system according to Example 8 of the present invention is illustrated in FIGS. 24 and 25. FIG. 25A illustrates an underwater observation state and FIG. 25B illustrates a state of observation in the air. An aberration diagram of the underwater observation state is shown in FIG. 26.

In the endoscope objective optical system of Example 8, the underwater image height Iw is substantially the same as that of Example 1 but the underwater view angle is 144.8°, which is wider than that in Example 1 by approximately 15° and is characterized in that the object side surface of the first lens is a convex surface. The endoscope objective optical system in Example 8 is composed of a first group composed of a concave meniscus lens with the convex surface directed to the object side (first lens), a second group composed of a plano-concave lens, a color correction filter, a brightness diaphragm, and a back group having a positive refractive power in order from the object side.

The back group is composed of three groups and all of them have the positive refractive power. The present invention has a design idea that protrusions or dents are not generated on the object side surface of the first lens, but since an effect of improving distortion in the underwater observation state can be obtained by having the convex surface, the convex surface satisfying the expression (3) was employed in Example 8.

The distortion in the underwater observation state in Example 8 is −61.7% at the maximum image height. The distortion when the image height was changed so that Example 1 with the planar object side surface has the same underwater view angle of this Example was −64.4%, and the barrel type distortion can be reduced by making the object side surface of the first lens a convex surface. In other Examples of the present invention in which the first lens is composed of a plano-convex lens, sapphire is assumed to be used for the first lens material, but in Example 8, general optical glass is assumed to be the first lens material in view of workability of the concave meniscus lens.

The lens data of the endoscope objective optical system according to Example 8 is shown below.
Lens Data

| Plane number | r | d | Nd | Vd |
|---|---|---|---|---|
| 1 | 7.004 | 0.30 | 1.88300 | 40.76 |
| 2 | 0.580 | 0.31 | | |
| 3 | ∞ | 0.25 | 2.00330 | 28.27 |
| 4 | 1.425 | 0.08 | | |
| 5 | ∞ | 0.30 | 1.52134 | 74.98 |
| 6 (STO) | ∞ | 0.05 | | |
| 7 | 3.968 | 0.99 | 1.80100 | 34.97 |
| 8 | −1.262 | 0.05 | | |
| 9 | 8.402 | 0.30 | 2.00330 | 28.27 |
| 10 | 1.298 | 0.89 | 1.72916 | 54.68 |
| 11 | −1.535 | 0.05 | | |
| 12 | 2.855 | 0.83 | 1.48749 | 70.23 |
| 13 | −1.161 | 0.30 | 1.92286 | 18.90 |
| 14 | −2.551 | 0.29 | | |
| 15 | ∞ | 1.10 | 1.51633 | 64.14 |
| 16 (image plane) | ∞ (IP) | | | |

Example 9

Figure 27:
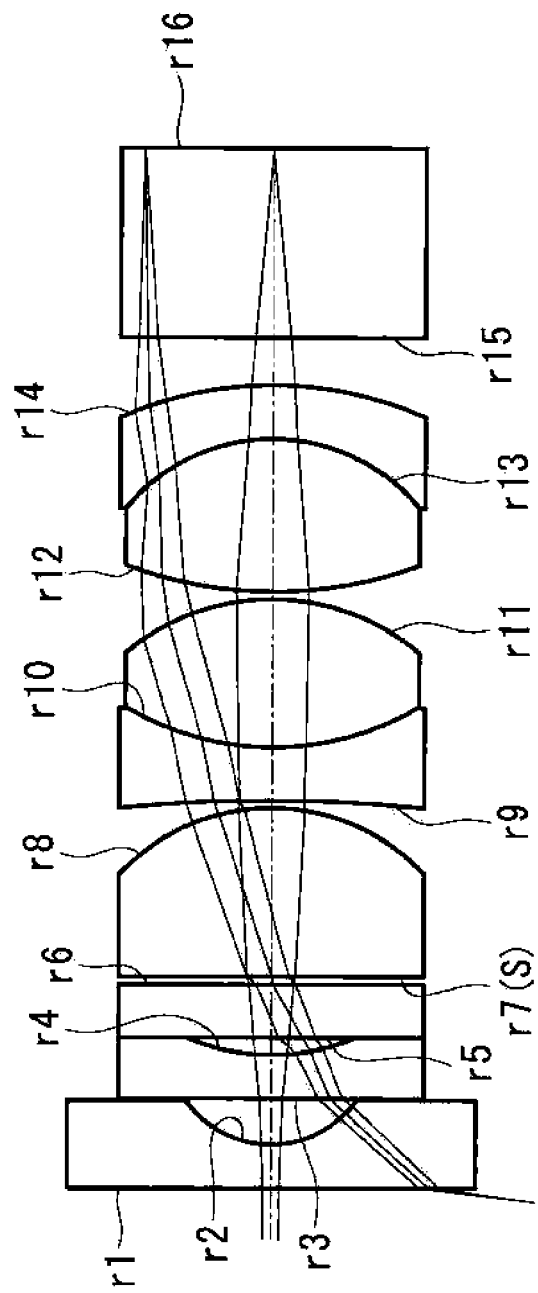
FIG. 27 is a sectional view illustrating the entire constitution of the endoscope objective optical system according to a ninth example of the present invention.

A lens constitution of the endoscope objective optical system according to Example 9 of the present invention is illustrated in FIGS. 27 and 28. FIG. 28A illustrates an underwater observation state and FIG. 28B illustrates a state of observation in the air. An aberration diagram of the underwater observation state is shown in FIG. 29.

The endoscope objective optical system of Example 9 has the widest underwater view angle in all the aforementioned Examples. The endoscope objective optical system of Example 9 is composed of a first group composed of a plano-concave lens (first lens), a second group composed of a plano-concave lens, a color correction filter, a brightness diaphragm assuming mounting on a thin plate, and a back group having a positive refractive power in order from the object side. The back group is composed of three groups, and all of them have the positive refractive power.

The underwater view angle of Example 9 is 164.4° and accordingly, Ia/Iw is 0.708, which is the smallest in Examples of the present invention. Example 9 has a super-wide angle at an unparalleled level as the endoscope objective optical system, but the outer diameter DL1 of the first lens is not so large at Ø2.4 mm and is an outer diameter of a level at which a thin-diameter endoscope with a treatment channel can be realized.

The lens data of the endoscope objective optical system according to Example 9 is shown below.
Lens Data

| Plane number | r | d | Nd | Vd |
|---|---|---|---|---|
| 1 | ∞ | 0.25 | 1.76820 | 71.79 |
| 2 | 0.639 | 0.27 | | |
| 3 | ∞ | 0.25 | 2.00330 | 28.27 |
| 4 | 1.522 | 0.11 | | |
| 5 | ∞ | 0.30 | 1.52134 | 74.98 |

-continued

| Plane number | r | d | Nd | Vd |
|---|---|---|---|---|
| 6 | ∞ | 0.03 | | |
| 7 (STO) | ∞ | 0.98 | 2.00330 | 28.27 |
| 8 | −1.243 | 0.05 | | |
| 9 | −7.985 | 0.30 | 2.00330 | 28.27 |
| 10 | 1.686 | 0.86 | 1.72916 | 54.68 |
| 11 | −1.322 | 0.05 | | |
| 12 | 2.582 | 0.87 | 1.48749 | 70.23 |
| 13 | −1.108 | 0.30 | 1.92286 | 18.90 |
| 14 | −2.366 | 0.28 | | |
| 15 | ∞ | 1.10 | 1.51633 | 64.14 |
| 16 (image plane) | ∞ | | | |

Various types of data in the constitutions of the aforementioned Examples 1 to 9 are shown in Table 2 and values relating to the aforementioned expressions (1) to (8) are shown in Table 3.

TABLE 2

<EXAMPLE LIST>

| EXAMPLE | ft [mm] | Fno. | OBJECT DISTANCE IN WATE [mm] | Iw [mm] | FOVw [°] | Ia [mm] | FOVa [°] | DL1 [mm] | fL1 [mm] | RL1 [mm] |
|---|---|---|---|---|---|---|---|---|---|---|
| 1 | 0.560 | 4.153 | 9.0 | 0.7510 | 129.4 | 0.5995 | 180.0 | 2.2 | −0.832 | ∞ |
| 2 | 0.487 | 4.652 | 7.0 | 0.6520 | 129.8 | 0.5195 | 180.0 | 2.2 | −0.832 | ∞ |
| 3 | 0.337 | 3.605 | 6.0 | 0.4480 | 129.6 | 0.3585 | 180.0 | 2.2 | −0.832 | ∞ |
| 4 | 0.676 | 5.488 | 8.0 | 0.9120 | 129.8 | 0.7301 | 180.0 | 2.2 | −0.832 | ∞ |
| 5 | 0.652 | 5.465 | 7.5 | 0.9120 | 139.8 | 0.7019 | 180.0 | 2.2 | −0.832 | ∞ |
| 6 | 0.670 | 5.582 | 8.0 | 0.9120 | 138.2 | 0.7128 | 180.0 | 2.3 | −0.832 | ∞ |
| 7 | 0.662 | 5.096 | 9.0 | 0.7512 | 105.0 | 0.7039 | 180.0 | 1.8 | −0.799 | ∞ |
| 8 | 0.498 | 4.040 | 8.0 | 0.7512 | 144.8 | 0.5868 | 189.6 | 2.4 | −0.732 | 7.004 |
| 9 | 0.498 | 4.092 | 8.0 | 0.7512 | 164.4 | 0.5321 | 180.0 | 2.4 | −0.832 | ∞ |

TABLE 3

| EXAMPLE | Iw/ft | Ia/Iw | |DL1/RL1a| | fL1/ft | Iw/DL1 |
|---|---|---|---|---|---|
| 1 | 1.341 | 0.798 | 0 | −1.486 | 0.341 |
| 2 | 1.339 | 0.797 | 0 | −1.710 | 0.296 |
| 3 | 1.329 | 0.800 | 0 | −2.471 | 0.204 |
| 4 | 1.349 | 0.801 | 0 | −1.231 | 0.415 |
| 5 | 1.399 | 0.770 | 0 | −1.276 | 0.415 |
| 6 | 1.361 | 0.782 | 0 | −1.242 | 0.397 |
| 7 | 1.135 | 0.937 | 0 | −1.207 | 0.417 |
| 8 | 1.508 | 0.781 | 0.343 | −1.507 | 0.313 |
| 9 | 1.508 | 0.708 | 0 | −1.670 | 0.313 |

Moreover, in the aforementioned aspect, the first lens is preferably a plano-concave lens having a planar object-side surface.

By constituting as above, the objective optical system with favorable workability and a low cost can be provided. In order to have the negative power as the entire first lens, the image side object is a concave surface, but any one of the plane, the convex surface, and the concave surface can be employed for the object side surface. The first lens is the most preferably the plano-concave lens from the viewpoint of workability and a cost, and a highly hard and hardly workable material such as sapphire with poor workability can be employed, and abrasion resistance can be improved.

Moreover, another aspect of the present invention provides an endoscope objective optical system used for the underwater observation and provided with a front group having a negative refractive power, a brightness diaphragm, and a back group having a positive refractive power in order from the object side, the front group is composed of a first group having the negative refractive power and a second group having the negative refractive power, the first group is a first lens which is a single lens, the second group is a single lens or a cemented lens and the following conditional expression being satisfied:

$$1<Iw/ft<1.8 \quad (5)$$

where Iw is the maximum image height in the underwater observation, and ft is the focal distance of the entire objective optical system in the observation in the air.

By constituting as above, a so-called retro-focus type composed of the negative front group-positive back group is constituted by sandwiching a brightness diaphragm and thus, angle widening and sufficient correction of field curvature in the underwater observation can be realized.

Specifically, since it is difficult to bear the negative refractive power of the front group only by one group depending on the underwater view angle, the front group is preferably divided into two negative groups, that is, the first group and the second group. The first group is preferably composed of a single lens which can be thinned. In the second group, an angle is relaxed by refraction in the first group, and a light beam height is lowered and thus, it may be composed of a single lens or a cemented lens.

By constituting as above and by satisfying the condition in the aforementioned expression (5), the endoscope objective optical system which has a sufficiently wide angle even in the underwater observation can be constituted as a realistic lens.

Moreover, in the aforementioned aspect, the following conditional expressions are preferably satisfied:

$$|DL1/RL1a|<0.4 \quad (6)$$

$$-3<fL1/ft<-1 \quad (7)$$

where DL1 is an outer diameter of the first lens, RL1a is a radius of curvature of an object side surface of the first lens, and fL1 is a focal distance of the first lens.

The aforementioned expression (6) is a condition for a constitution that a degree of convex and concave on the first lens object side surface is made small and relatively close to a plane. If the first group is made of flat plates, for example, a light beam which can be transmitted through an image side surface of a flat plate in contact with the air has the same angle as that of the object side surface in a state of observation in the air and thus, Iw cannot be made larger than Ia. Since a light flux at an extremely large angle passes through the first group, a lens thickness is closely related with a light beam height, and if the thickness is increased, the lens outer diameter is increased. Thus, it is necessary that use of cemented lenses with increased lens thickness is avoided so as to promote thinning by using a single lens for the first group.

If the upper limit of the aforementioned expression (6) is exceeded on the convex surface, the convex from a lens outer diameter end becomes too large, and a mechanical design to avoid lens breakage or illumination light incidence becomes difficult. Moreover, if the upper limit of the aforementioned expression (6) is exceeded on the concave surface, the concave from the lens outer diameter end becomes too large, and deterioration in cleaning performance or an increase of Fresnel reflective rate in the peripheral portion of the concave surface occurs.

The expression (7) is a condition relating to the focal distance of the first lens. Not only in order to give the first lens the negative power but also to have an absolute amount of the power within an appropriate range, the expression (7) needs to be satisfied. If the lower limit of the expression (7) is not reached, the power is so weak that the angle in the water cannot be widened easily, while if the upper limit of the expression (7) is exceeded, the negative power is so strong that an excessive correction tendency of field curvature occurs.

Moreover, in the aforementioned aspect, the first lens is preferably a plano-concave lens having a planar object-side surface.

By constituting as above, the objective optical system with favorable workability and a low cost can be provided.

Advantageous Effects of Invention

According to the present invention, such effects are exerted that a view angle is wide even in the underwater observation, reliability as a medical endoscope is ensured, and mounting design can be made easily.

REFERENCE SIGNS LIST

GF front group
GB back group
G1 first lens group
G2 second lens group
L1 first lens
L2 second lens
L3 third lens
L4 fourth lens
L5 fifth lens
L6 sixth lens
L7 seventh lens

The invention claimed is:

1. An endoscope objective optical system used for underwater observation comprising:
a front group having a negative refractive power, a brightness diaphragm, and a back group having a positive refractive power in order from an object side, wherein
the back group is composed of three groups, all of the three groups having the positive refractive power;
the front group is composed of a first group having a negative refractive power and a second group having a negative refractive power;
the first group is a first lens which is a single lens;
the second group is a single lens or a cemented lens; and
conditional expressions below are satisfied:

$$1 < Iw/ft < 1.8 \tag{1}$$

$$0.6 < Ia/Iw < 0.95 \tag{2}$$

$$|DL1/RL1a| < 0.4 \tag{3}$$

$$-3 < fL1/ft < -1 \tag{4}$$

where Iw is a maximum image height in the underwater observation, ft is a focal distance of an entire objective optical system in observation in the air, Ia is a maximum image height of a principal ray that is capable of being transmitted through an objective optical system during the observation in the air, DL1 is an outer diameter of the first lens, RL1a is a radius of curvature of an object side surface of the first lens, and fL1 is a focal distance of the first lens.

* * * * *